United States Patent
Daubresse et al.

(10) Patent No.: US 7,717,964 B2
(45) Date of Patent: May 18, 2010

(54) STYRYL THIOL/DISULFIDE COMPOUND WITH A HYDROXY(CYCLO)ALKYLAMINO UNIT, PROCESS FOR LIGHTENING KERATIN MATERIALS USING SAME

(75) Inventors: Nicolas Daubresse, la Celles St Cloud (FR); Andrew Greaves, Montevrain (FR); Franco Manfre, le Perreux sur Marne (FR)

(73) Assignee: L'Oreal S.A., Paris (FR)

( * ) Notice: Subject to any disclaimer, the term of this patent is extended or adjusted under 35 U.S.C. 154(b) by 53 days.

(21) Appl. No.: 12/234,001

(22) Filed: Sep. 19, 2008

(65) Prior Publication Data

US 2009/0172897 A1 Jul. 9, 2009

Related U.S. Application Data

(60) Provisional application No. 60/960,677, filed on Oct. 10, 2007.

(30) Foreign Application Priority Data

Sep. 21, 2007 (FR) .................................. 07 57755

(51) Int. Cl.
*A61Q 5/10* (2006.01)
*C07C 321/00* (2006.01)
(52) U.S. Cl. ........................ 8/405; 8/431; 8/465; 8/568; 8/587; 8/648; 562/426
(58) Field of Classification Search ...................... 8/405, 8/431, 465, 568, 587, 648; 462/426
See application file for complete search history.

(56) References Cited

U.S. PATENT DOCUMENTS

| 2,904,385 | A | 9/1959 | Roger et al. |
| 4,823,985 | A | 4/1989 | Grollier et al. |
| 7,147,673 | B2 | 12/2006 | Plos et al. |
| 7,150,764 | B2 | 12/2006 | Plos et al. |
| 7,186,278 | B2 | 3/2007 | Plos et al. |
| 7,192,454 | B2 | 3/2007 | Plos et al. |
| 7,195,650 | B2 | 3/2007 | Plos et al. |
| 7,195,651 | B2 | 3/2007 | Plos et al. |

(Continued)

FOREIGN PATENT DOCUMENTS

BE 669 934 1/1966

(Continued)

OTHER PUBLICATIONS

STIC Search Report dated Dec. 7, 2009.*

(Continued)

*Primary Examiner*—Eisa B Elhilo
(74) *Attorney, Agent, or Firm*—Finnegan Henderson Farabow Garrett & Dunner L.L.P.

(57) ABSTRACT

The disclosure relates to the dyeing of keratin materials using styryl hydroxy(cyclo)alkylamino thiol/disulfide fluorescent dyes. Disclosed herein is a dye composition comprising a styryl hydroxy(cyclo)alkylamino thiol/disulfide fluorescent dye and a dyeing process with, for example, a lightening effect on keratin materials such as hair, using said composition. Disclosed herein are novel thiol/disulfide fluorescent dyes and the uses thereof in lightening keratin materials. This composition makes it possible to obtain a lightening effect which can be resistant and visible on dark keratin fibers.

19 Claims, 1 Drawing Sheet

U.S. PATENT DOCUMENTS

Figure 1:
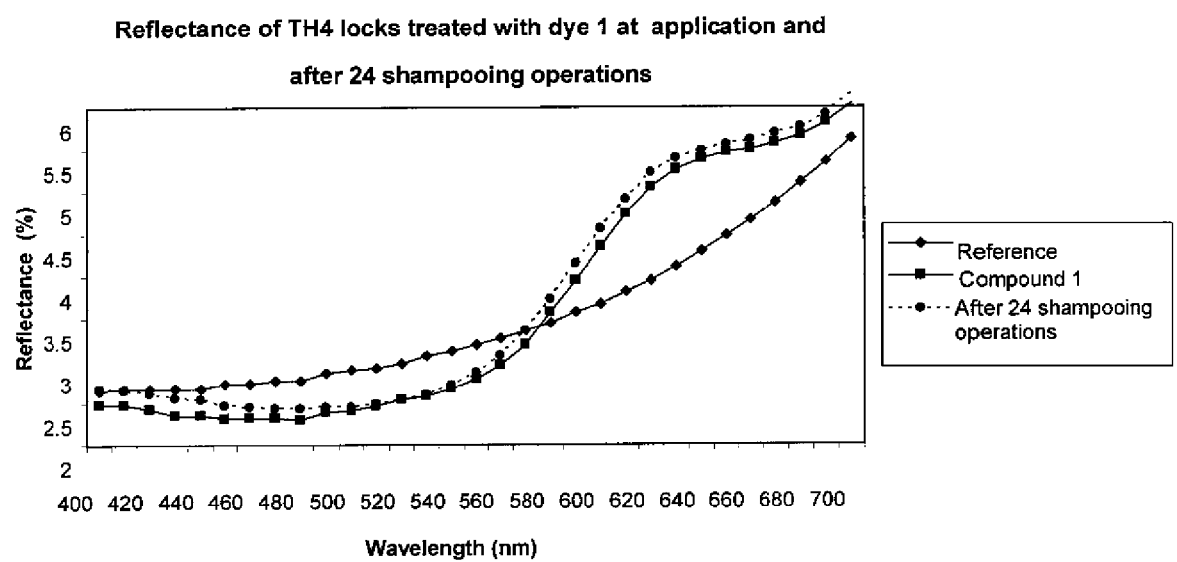

| | | | |
|---|---|---|---|
| 7,198,650 | B2 | 4/2007 | Pourille-Grethen et al. |
| 7,204,860 | B2 | 4/2007 | Plos et al. |
| 7,208,018 | B2 | 4/2007 | Gourlaouen et al. |
| 7,217,296 | B2 | 5/2007 | Pastore et al. |
| 7,250,064 | B2 | 7/2007 | Plos et al. |
| 7,261,744 | B2 | 8/2007 | Gourlaouen et al. |
| 7,276,086 | B2 | 10/2007 | Gourlaouen |
| 7,303,589 | B2 | 12/2007 | Greaves et al. |
| 7,377,946 | B2 | 5/2008 | Gourlaouen et al. |
| 7,488,354 | B2 | 2/2009 | Daubress et al. |
| 7,531,008 | B2 | 5/2009 | Lagrange |
| 7,544,215 | B2 | 6/2009 | Speckbacher et al. |
| 2003/0176316 | A1 | 9/2003 | Whitehead et al. |
| 2004/0253757 | A1 | 12/2004 | Gourlaouen et al. |
| 2005/0031563 | A1 | 2/2005 | Gourlaouen et al. |
| 2007/0231940 | A1 | 10/2007 | Gourlaouen et al. |
| 2009/0049621 | A1 | 2/2009 | Greaves et al. |
| 2009/0089939 | A1 | 4/2009 | Greaves et al. |
| 2009/0126125 | A1 | 5/2009 | Greaves et al. |
| 2009/0126755 | A1 | 5/2009 | Guerin et al. |

FOREIGN PATENT DOCUMENTS

| | | |
|---|---|---|
| EP | 0 860 636 | 8/1998 |
| EP | 1 464 321 | 10/2004 |
| EP | 1 464 323 | 10/2004 |
| EP | 1 464 324 | 10/2004 |
| EP | 1 647 580 | 4/2006 |
| EP | 1 792 605 | 6/2007 |
| EP | 2 001 960 | 12/2008 |
| EP | 2 004 757 | 12/2008 |
| EP | 2 018 847 | 1/2009 |
| EP | 2 062 945 | 5/2009 |
| FR | 1 156 407 | 5/1958 |
| FR | 2 586 913 | 3/1987 |
| FR | 2 830 189 | 4/2003 |
| FR | 2 830 194 | 4/2003 |
| FR | 2 850 271 | 7/2004 |
| FR | 2 921 381 | 3/2009 |
| FR | 2 921 377 | 6/2009 |
| GB | 2 143 541 | 2/1985 |
| GB | 2 180 215 | 3/1987 |
| WO | WO 96/041173 | 12/1996 |
| WO | WO 99/51194 | 10/1999 |
| WO | WO 03/028685 | 4/2003 |
| WO | WO 2004/091473 | 10/2004 |
| WO | WO 2004/091556 | 10/2004 |
| WO | WO 2005/004822 | 1/2005 |
| WO | WO 2005/075574 | 8/2005 |
| WO | WO 2005/097051 | 10/2005 |
| WO | WO 2006/060533 | 6/2006 |
| WO | WO 2006/134043 | 12/2006 |
| WO | WO 2006/134043 A2 * | 12/2006 |
| WO | WO 2006/136617 | 12/2006 |
| WO | WO 2007/025889 | 3/2007 |
| WO | WO 2007/039527 | 4/2007 |
| WO | WO 2007/110537 | 10/2007 |
| WO | WO 2007/110539 | 10/2007 |
| WO | WO 2007/110542 | 10/2007 |
| WO | WO 2009/037324 | 3/2009 |
| WO | WO 2009/037348 | 3/2009 |
| WO | WO 2009/037350 | 3/2009 |
| WO | WO 2009/037385 | 3/2009 |
| WO | WO 2009/040354 | 4/2009 |
| WO | WO 2009/040355 | 4/2009 |

OTHER PUBLICATIONS

Okawa, et al., "Synthesis and Characterization of an Alkanethiol Thin Film Containing a Hemicyanine Dye," Molecular Crystals and Liquid Crystals Science and Technology, vol. 377, Jan. 1, 2002, pp. 137-140.

French Search Report for FR 07/57755, dated Jul. 30, 2008.
Ashwell, G. et al., "Improved Molecular Rectification from Self-Assembled Monolayers of a Sterically Hindered Dye," Journal of the American Chemical Society, vol. 127, No. 46, (2005), pp. 16238-16244.
Ashwell, G. et al., "Induced Rectification from Self-Assembled Monolayers of Sterically Hindered-Bridged Chromophores," Journal of Materials Chemistry, vol. 15, No. 11, (2005), pp. 1160-1166.
Ashwell, G. et al., "Molecular Rectification: Self-Assembled Monolayers of a Donor Acceptor Chromophore Connected via a Truncated Bridge," Journal of Materials Chemistry, vol. 13, No. 12, (2003), pp. 2855-2857.
Copending U.S. Appl. No. 12/233,955, filed Sep. 19, 2008.
Copending U.S. Appl. No. 12/234,072, filed Sep. 19, 2008.
Copending U.S. Appl. No. 12/234,135, filed Sep. 19, 2008.
Copending U.S. Appl. No. 12/282,586, filed Sep. 11, 2008.
Copending U.S. Appl. No. 12/293,684, filed Sep. 19, 2008.
Copending U.S. Appl. No. 12/293,723, filed Sep. 19, 2008.
Copending U.S. Appl. No. 12/293,955, filed Sep. 22, 2008.
English language Abstract of EP 1 464 323, dated Oct. 6, 2004.
English language Abstract of EPp 2 001 960, dated Dec. 17, 2008.
English language Abstract of EP 2 004 757, dated Dec. 24, 2008.
English language Abstract of EP 2 018 847, dated Jan. 28, 2009.
English language Abstract of EP 2 062 945, dated May 27, 2009.
English language Abstract of FR 2 921 377, dated Jun. 17, 2009.
English language Abstract of FR 2 921 381, dated Mar. 27, 2009.
English language Abstract of WO 2007/110537, dated Oct. 4, 2007.
English language Abstract of WO 2007/110539, dated Oct. 4, 2007.
English language Abstract of WO 2007/110542, dated Oct. 4, 2007.
European Search Report for EP 08 16 4735, dated May 19, 2009.
French Search Report for FR 07/57753, dated Aug. 4, 2008.
French Search Report for FR 07/57773, dated Jul. 7, 2008.
French Search Report for FR 07/57778, dated Aug. 20, 2008.
International Search Report for PCT/FR2007/050997, dated Jun. 19, 2008.
International Search Report for PCT/FR2007/051003, dated Feb. 19, 2008.
International Search Report for PCT/FR2007/051005, dated May 6, 2008.
International Search Report for PCT/FR2007/051008, dated Feb. 5, 2008.
IP.com document dated Oct. 13, 2005.
Kajikawa, K. et al., "Preparation and Optical Characterization of Hemicyanine Self-Assembled Monolayer on Au Substrate," Molecular Crystals and Liquid Crystals Science and Technology, vol. 370, (2001), pp. 277-283.
Naraokaa, R. et al., "Nonlinear Optical Property of Hemicyanine Self-Assembled Monolayers on Gold and its Absorption Kinetics Probed by Optical Second-Harmonic Generation and Surface Plasmon Resonance Spectroscopy," Chemical Physics Letters, vol. 362, No. 1-2, (2002), pp. 26-30.
Notice of Allowance mailed May 4, 2009, in co-pending U.S. Appl. No. 12/234,135.
Notice of Allowance mailed Sep. 3, 2009, in co-pending U.S. Appl. No. 12/234,135.
Office Action mailed Apr. 28, 2009, in co-pending U.S. Appl. No. 12/234,072.
STIC Search Report for U.S. Appl. No. 12/234,072, dated Apr. 23, 2009.
STIC Search Report dated Apr. 27, 2009, for U.S. Appl. No. 12/234,135.
Tsuboi, K. et al., "Formation of Merocyanine Self-Assembled Monolayer and its Nonlinear Optical Properties Probed by Second-Harmonic Generation and Surface Plasmon Resonance," Japanese Journal of Applied Physics, vol. 42, No. 2A, (2003), pp. 607-613.
Wang, Y. et al., "Synthesis and Fluorescence Properties of Triad Compounds with Aromatic Sulfur Bridges," Dyes and Pigments, vol. 51, No. 2-3, (2001), pp. 127-136.
Wang, Y. et al., "Synthesis and Luminescence Properties of Triad Compounds with a Disulfide Bridge," vol. 54, No. 3, (2002), pp. 265-274.

* cited by examiner

STYRYL THIOL/DISULFIDE COMPOUND WITH A HYDROXY(CYCLO)ALKYLAMINO UNIT, PROCESS FOR LIGHTENING KERATIN MATERIALS USING SAME

This application claims benefit of U.S. Provisional Application No. 60/960,677, filed Oct. 10, 2007, the contents of which are incorporated herein by reference. This application also claims benefit of priority under 35 U.S.C. §119 to French Patent Application No. FR 0757755, filed Sep. 21, 2007, the contents of which are also incorporated herein by reference.

The present disclosure relates to the dyeing of keratin materials using styryl hydroxy(cyclo)alkylamino thiol/disulfide fluorescent dyes.

It is well known to dye keratin fibers, such as human keratin fibers, by direct dyeing. The process conventionally used in direct dyeing comprises applying to the keratin fibers direct dyes which are colored or coloring molecules having an affinity for the fibers, allowing them to diffuse, and then rinsing the fibers.

The direct dyes which are conventionally used are, for example, dyes of the nitrobenzene type, anthraquinone dyes, nitropyridine dyes, or dyes of the azo, xanthene, acridine, azine, or triarlymethane type. The coloring of keratin fibers using these conventional direct dyes does not make it possible to significantly lighten keratin fibers.

The lightening of the color of dark keratin fibers to lighter shades, by optionally modifying the shade thereof, constitutes an important demand.

Conventionally, in order to obtain a lighter coloring, a chemical bleaching process is used. This process comprises treating the keratin fibers, such as hair, with a strong oxidizing system, generally composed of hydrogen peroxide, possibly in combination with persalts, generally in an alkaline medium.

This bleaching system has the drawback of damaging the keratin fibers and of detrimentally affecting their cosmetic properties. The fibers in fact have a tendency to become rough, more difficult to disentangle, and more brittle. Finally, the lightening or the bleaching of keratin fibers with oxidizing agents is incompatible with the treatments for modifying the shape of said fibers, such as in hair straightening treatments.

Another lightening technique comprises applying fluorescent direct dyes to dark hair. This technique, described for instance in International Patent Application Publication Nos. WO 03/028685 and WO 2004/091473, makes it possible to retain the quality of the keratin fiber during the treatment. However, these fluorescent direct dyes do not exhibit satisfactory fastness with respect to outside agents.

In order to increase the fastness of direct colorings, it is known to use disulfide dyes, such as aza-imidazolium chromophore dyes described in International Patent Application Publication No. WO 2005/097051 or European Patent Application Publication No. EP 1647580, and pyridinium/indolinium styryl chromophore dyes described in International Patent Application Publication Nos. WO 2006/134043 and WO 2006/136617.

The aim of the present disclosure is to provide new systems for dyeing keratin materials, such as human keratin fibers, for example hair, which do not have the drawbacks of the existing bleaching processes.

For example, one aim of the disclosure is to provide direct dyeing systems for obtaining lightening effects, especially on naturally or artificially dark keratin fibers, which are resistant to successive shampooing operations, which do not damage the keratin fibers, and which do not detrimentally affect their cosmetic properties.

Another aim of the disclosure is to dye keratin materials chromatically and in a manner which is persistent with respect to outside attacks. The disclosure also aims to provide compounds which dye keratin fibers such as hair with a low dyeing selectivity between the root and the end, whether on natural fibers or permanent-waved fibers.

These aims can be achieved with the present disclosure, a subject of which is a process for dyeing keratin materials, such as keratin fibers, for example human keratin fibers such as hair, for example dark hair, comprising applying, to the keratin materials, a dye composition comprising, in a suitable cosmetic medium, at least one disulfide or thiol fluorescent dye, chosen from the dyes of formula (I) below:

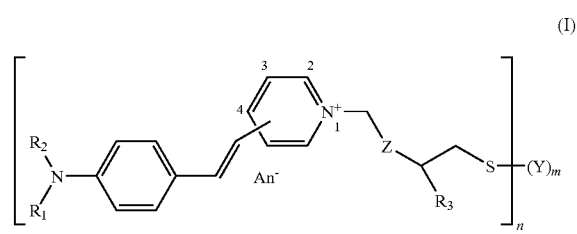

the organic or mineral acid salts, optical isomers and geometric isomers thereof, and the solvates such as hydrates:

wherein in formula (I):

$R_1$ is chosen from a $C_1$-$C_6$ alkyl group substituted with at least one hydroxyl group or —C(O)OR' group, wherein R' is chosen from a hydrogen atom, a $C_1$-$C_4$ alkyl group and a —C(O)—O⁻ group, and when R' is a —C(O)—O⁻ group an anionic counterion An⁻ is absent;

$R_2$ is chosen from a $C_1$-$C_6$ alkyl group optionally substituted with at least one hydroxyl group;

or else the groups $R_1$ and $R_2$ form, together with the nitrogen which bears them, a saturated heterocyclic radical substituted at least with a hydroxyl, (poly)hydroxy($C_1$-$C_4$)alkyl, and/or —C(O)OR' group, with R' representing a hydrogen atom, a $C_1$-$C_4$ alkyl group or else a —C(O)—O⁻ group, and when R' is a —C(O)—O⁻ group an anionic counterion An⁻ is absent;

$R_3$ is chosen from a hydrogen atom or a —C(O)OR" group, wherein R" is chosen from a hydrogen atom, an alkali metal or a $C_1$-$C_6$ alkyl group, or else $R_3$ comprises a —C(O)—O⁻ group and, in this case, an anionic counterion An⁻ is absent;

Z is chosen from a divalent amido —C(O)—N(R)— or —N(R)—C(O)— group, or a divalent $C_1$-$C_{10}$ alkylene group interrupted with an amido —C(O)—N(R)— or —N(R)—C(O)— group, wherein R is chosen from a hydrogen atom or a $C_1$-$C_6$ alkyl group;

n is an integer ranging from 1 to 2;

m is an integer ranging from 0 to 1;

An⁻ represents an anionic counterion;

Y is chosen from: i) a hydrogen atom, ii) an alkali metal, iii) an alkaline earth metal, iv) an ammonium group: N⁺R^α R^β R^γ R^δ, wherein R^α, R^β, R^γ and R^δ, which may be identical or different, are chosen from a hydrogen atom or a ($C_1$-$C_4$)alkyl group, v) a phosphonium group: P⁺R^α R^β R^γ R^δ, wherein R^α, R^β, R^γ and R^δ, which may be identical or different, are chosen from a hydrogen atom or a ($C_1$-$C_4$)alkyl group, or vi) a thiol-function-protecting group;

wherein:
the bond between the pyridinium ring and the double bond of the styryl group is positioned in the 2- or 4-position with respect to the pyridinium;

when n=1, m=1, then Y=H or a thiol-function-protecting group, and when n=2, then m=0; and when the compound of formula (I) comprises other cationic parts, it is associated with one or more anionic counterions which allow formula (I) to achieve electroneutrality.

In certain embodiments according to this disclosure, $R_1$ is chosen from a $C_1$-$C_6$ alkyl group substituted with a single hydroxyl group. In certain embodiments according to this disclosure, $R_2$ is chosen from a $C_1$-$C_6$ alkyl group optionally substituted with one or more hydroxyl groups. In other embodiments according to this disclosure, the groups $R_1$ and $R_2$ form, together with the nitrogen which bears them, a saturated heterocyclic radical chosen from pyrrolidinyl and piperidyl.

In certain embodiments according to this disclosure, Z is chosen from $(CH_2)_{n'}$—$C(O)$—$N(R)$—$(CH_2)_p$— or —$(CH_2)_{n''}$—$N(R)$—$C(O)$—$(CH_2)_p$—, wherein n' is an integer ranging from 0 to 3; p is an integer ranging from 0 to 4, n" is an integer ranging from 0 to 3. In some embodiments, n' is chosen from 0, 2, or 3. In some embodiments, n'=n"=p=0.

As used herein, the limits delimiting the extent of the range of values are included in this range of values.

Also disclosed herein is a dye composition comprising, in a suitable cosmetic medium, at least one thiol/disulfide fluorescent dye (I) as defined above, and optionally a reducing agent.

Another subject of the disclosure is novel thiol/disulfide fluorescent dyes of formula (I).

The dyeing process disclosed herein can make it possible to visibly color dark keratin materials, such as dark human keratin fibers, for example dark hair.

Furthermore, the process disclosed herein can make it possible to obtain a coloring of keratin materials, such as human keratin fibers, for example hair, without damaging said material, and which is persistent with respect to shampooing operations, common attacks (sunlight, perspiration), and other hair treatments. The process disclosed herein also can make it possible to obtain lightening of keratin materials such as keratin fibers, for example dark keratin fibers, such as dark hair.

The novel dyes disclosed herein can have very satisfactory photostability and chemical stability. These dyes are soluble in the cosmetic media suitable for hair dyeing, such as water/ethanol mixtures. They can make it possible to extend the accessible color range (yellow, orange, red colors) while at the same time leaving it possible to strip the colorings obtained.

After application to keratin fibers, the dyes of formula (I) dye the keratin materials chromatically and in a manner which can be persistent with respect to outside attacks, and with low dyeing selectivity between the root and the end, and on various types of fibers.

For the purpose of the present disclosure, the term "dark keratin material" means keratin material that exhibits a lightness L* measured in the C.I.E. L*a*b* system of less than or equal to 45, such as less than or equal to 40, given that L*=0 is equivalent to black and L*=100 is equivalent to white.

For the purpose of the disclosure, the expression "naturally or artificially dark hair" means hair whose tone height is less than or equal to 6 (dark blond), for example less than or equal to 4 (chestnut-brown).

The lightening of the hair is evaluated by the variation in "tone height" before and after application of the compound of formula (I). The notion of "tone" is based on the classification of the natural shades, one tone separating each shade from the shade immediately following or preceding it. This definition and the classification of the natural shades are well known to hair styling professionals and are published in the book "Science des traitements capillaires" [Hair Treatment Sciences], by Charles Zviak 1988, published by Masson, pp. 215 and 278.

The tone heights range from 1 (black) to 10 (very light blond), one unit corresponding to one tone; the higher the figure, the lighter the shade.

An artificially colored hair is a hair whose color has been modified by a dyeing treatment, for example dyeing with direct dyes or oxidation dyes.

For the purpose of the disclosure, the term "bleached hair" means hair whose tone height is greater than 6, for example greater than 7.

For the purpose of the disclosure, the term "stripping" the coloring of keratin fibers means a process which involves the application of a chemical or physical stimulus capable of returning the hair to its original color. By way of example, the stripping may be obtained by application of an oxidizing composition based on hydrogen peroxide, sodium persulfate, potassium persulfate, or ammonium persulfate, at a moderately alkaline pH, i.e. ranging from 7 to 12, such as from 8 to 10.5.

One means for measuring the lightening effect given to the hair after application of the fluorescent dyes disclosed herein is to use the phenomenon of hair reflectance.

The composition disclosed herein should, after application to dark hair, lead to at least one of the results below:

Interest is focused on the hair reflectance performance levels when said hair is irradiated with visible light in the wavelength range from 400 to 700 nanometers.

The curves of reflectance as a function of wavelength, of the hair treated with the composition of the disclosure and of untreated hair, are then compared.

The curve corresponding to the treated hair should show a reflectance in the wavelength range of from 500 to 700 nanometers, which is higher than the curve corresponding to the untreated hair.

This means that, in the wavelength range of from 540 to 700 nanometers, there is at least one range where the reflectance curve corresponding to the treated hair is higher than the reflectance curve corresponding to the untreated hair. The term "higher" means a difference of at least 0.05% in reflectance, such as at least 0.1%. All the same, there may be, in the wavelength range of from 540 to 700 nanometers, at least one range where the reflectance curve corresponding to the treated hair is superimposable on or lower than the reflectance curve corresponding to the untreated hair.

For example, the wavelength where the difference is at a maximum between the reflectance curve of the treated hair and that of the untreated hair is within the wavelength range of from 500 to 650 nanometers, such as within the wavelength range of from 550 to 620 nanometers.

For the purpose of the present disclosure, and unless otherwise indicated, the "aryl" or "heteroaryl" radicals, or the aryl or heteroaryl part of a radical, may be substituted with at least one substituent borne by a carbon atom, chosen from:

a $C_1$-$C_{16}$ alkyl radical, such as a $C_1$-$C_8$ alkyl radical, optionally substituted with one or more radicals chosen from the radicals: hydroxyl, $C_1$-$C_2$ alkoxy, $C_2$-$C_4$(poly)hydroxyalkoxy, acylamino and amino substituted with two $C_1$-$C_4$ alkyl radicals, which may be identical or different, optionally bearing at least one hydroxyl group, or the two radicals possibly forming, with the nitrogen atom to which they are attached, a heterocycle comprising from 5 to 7 members, such as 5 or 6 members, which is saturated or unsaturated, which is optionally substituted, and which optionally comprises another heteroatom which may be identical or different from the nitrogen;
  a halogen atom such as chlorine, fluorine or bromine;
  a hydroxyl group;
  a $C_1$-$C_2$ alkoxy radical;
  $C_1$-$C_2$ alkylthio radical;
  a $C_2$-$C_4$ (poly)hydroxyalkoxy radical;
  an amino radical;
  a 5- or 6-membered heterocycloalkyl radical;
  an optionally cationic 5- or 6-membered heteroaryl radical, such as imidazolium, optionally substituted with a $C_1$-$C_4$ alkyl radical, such as methyl;
  an amino radical substituted with one or two $C_1$-$C_6$ alkyl radicals, which may be identical or different, optionally bearing at least:
    i) one hydroxyl group, and/or
    ii) one amino group optionally substituted with one or two optionally substituted $C_1$-$C_3$ alkyl radicals, said alkyl radicals possibly forming, with the nitrogen atom to which they are attached, a heterocycle comprising from 5 to 7 members, which is saturated or unsaturated, which is optionally substituted, and which optionally comprises at least one other heteroatom which may or may not be different from nitrogen,
  —NR—COR' wherein the R radical is chosen from a hydrogen atom or a $C_1$-$C_4$ alkyl radical optionally bearing at least one hydroxyl group, and the R' radical chosen from a $C_1$-$C_2$ alkyl radical;
  $(R)_2N$—CO— wherein the R radicals, which may or may not be identical, are chosen from a hydrogen atom, or a $C_1$-$C_4$ alkyl radical optionally bearing at least one hydroxyl group;
  $R'SO_2$—NR— wherein the R radical is chosen from a hydrogen atom or a $C_1$-$C_4$ alkyl radical optionally bearing at least one hydroxyl group, and the R' radical is chosen from a $C_1$-$C_4$ alkyl radical or a phenyl radical;
  $(R)_2N$—$SO_2$— wherein the R radicals, which may or may not be identical, are chosen from a hydrogen atom or a $C_1$-$C_4$ alkyl radical optionally bearing at least one hydroxyl group,
  a carboxylic radical in acid or salified form (such as with an alkali metal or an ammonium, which is substituted or unsubstituted);
  a cyano group; and
  a polyhaloalkyl group comprising from 1 to 6 carbon atoms and from 1 to 6 halogen atoms, which may be identical or different; the polyhaloalkyl group can be, for example, trifluoromethyl.

For the purpose of the present disclosure, and unless otherwise indicated, the cyclic or heterocyclic part of a nonaromatic radical may be substituted with at least one substituent borne by a carbon atom, chosen from the groups:
  hydroxyl;
  $C_1$-$C_4$ alkoxy;
  $C_2$-$C_4$ (poly)hydroxyalkoxy;
  a $C_1$-$C_2$ alkylthio radical;
  RCO—NR'— wherein the R' radical is chosen from a hydrogen atom or a $C_1$-$C_4$ alkyl radical optionally bearing at least one hydroxyl group, and the R radical is chosen from a $C_1$-$C_2$ alkyl radical or an amino radical substituted with two $C_1$-$C_4$ alkyl groups, which may be identical or different, optionally bearing at least one hydroxyl group;
  RCO—O— wherein the R radical is chosen from a $C_1$-$C_4$ alkyl radical or an amino radical substituted with one or two $C_1$-$C_4$ alkyl groups, which may be identical or different, optionally bearing at least one hydroxyl group, said alkyl radicals possibly forming, with the nitrogen atom to which they are attached, a heterocycle comprising from 5 to 7 members, which is saturated or unsaturated, which is optionally substituted, and which optionally comprises at least one other heteroatom which may or may not be different from nitrogen; and
  RO—CO— wherein the R radical is chosen from a $C_1$-$C_4$ alkyl radical optionally bearing at least one hydroxyl group.

For the purpose of the present disclosure, and unless otherwise indicated, a cyclic or heterocyclic radical or a nonaromatic part of an aryl or heteroaryl radical may also be substituted with one or more oxo or thioxo groups.

For the purpose of the present disclosure, and unless otherwise indicated, an "aryl" radical comprises a carbon-based condensed or noncondensed, monocyclic or polycyclic group comprising from 6 to 22 carbon atoms, and at least one ring of which is aromatic; for example, the aryl radical is a phenyl, biphenyl, naphthyl, indenyl, anthracenyl or tetrahydronaphthyl.

For the purpose of the present disclosure, and unless otherwise indicated, a "diarylalkyl" radical comprises a group comprising, on the same carbon atom of an alkyl group, two aryl groups, which may be identical or different, such as diphenylmethyl or 1,1-diphenylethyl.

For the purpose of the present disclosure, and unless otherwise indicated, a "heteroaryl radical" comprises an optionally cationic, condensed or noncondensed, monocyclic or polycyclic group comprising from 5 to 22 members and from 1 to 6 heteroatoms chosen from a nitrogen, oxygen, sulfur and selenium atom, and at least one ring of which is aromatic; for example, a heteroaryl radical is chosen from acridinyl, benzimidazolyl, benzobistriazolyl, benzopyrazolyl, benzopyridazinyl, benzoquinolyl, benzothiazolyl, benzotriazolyl, benzoxazolyl, pyridinyl, tetrazolyl, dihydrothiazolyl, imidazopyridinyl, imidazolyl, indolyl, isoquinolyl, naphthoimidazolyl, naphthooxazolyl, naphthopyrazolyl, oxadiazolyl, oxazolyl, oxazolopyridyl, phenazinyl, phenooxazolyl, pyrazinyl, pyrazolyl, pyrilyl, pyrazoyltriazyl, pyridyl, pyridinoimidazolyl, pyrrolyl, quinolyl, tetrazolyl, thiadiazolyl, thiazolyl, thiazolopyridinyl, thiazoylimidazolyl, thiopyrylyl, triazolyl, xanthylyl and its ammonium salt.

For the purpose of the present disclosure, and unless otherwise indicated, a "diheteroarylalkyl" radical comprises a group comprising, on the same carbon atom of an alkyl group, two heteroaryl groups, which may be identical or different, such as difurylmethyl, 1,1-difurylethyl, dipyrrolylmethyl or dithienylmethyl.

For the purpose of the present disclosure, and unless otherwise indicated, a "cyclic radical" comprises a condensed or noncondensed, monocyclic or polycyclic, nonaromatic cycloalkyl radical comprising from 5 to 22 carbon atoms, possibly comprising one or more unsaturations; for example, the cyclic radical is a cyclohexyl.

For the purpose of the present disclosure, and unless otherwise indicated, a "sterically hindered cyclic" radical comprises a substituted or unsubstituted, aromatic or nonaromatic, cyclic radical hindered by steric effect or constraint, comprising from 6 to 14 members, which may be bridged; by way of sterically hindered radicals, for example: bicyclo [1.1.0]butane, mesityls such as 1,3,5-trimethylphenyl, 1,3,5-tri-tert-butylphenyl, 1,3,5-isobutylphenyl, 1,3,5-trimethylsilylphenyl and adamantyl.

For the purpose of the present disclosure, and unless otherwise indicated, a "heterocyclic radical or heterocycle" comprises a condensed or noncondensed, monocyclic or polycyclic, nonaromatic radical comprising from 5 to 22 members, comprising from 1 to 6 heteroatoms chosen from nitrogen, oxygen, sulfur and selenium; for example, the radical is monocyclic and comprises from 5 to 7 ring members and 1 or 2 heteroatoms chosen from nitrogen, oxygen and sulfur, of which at least one of the heteroatoms is a nitrogen atom; for example, the heterocyclic radical is chosen from pyrrolidinyl and piperidyl.

For the purpose of the present disclosure, and unless otherwise indicated, an "alkyl radical" comprises a linear or branched, $C_1$-$C_{16}$ hydrocarbon-based radical, such as a $C_1$-$C_8$, hydrocarbon-based radical.

For the purpose of the present disclosure, and unless otherwise indicated, the expression "optionally substituted" assigned to the alkyl radical means that said alkyl radical may be substituted with one or more radicals chosen from the radicals: i) hydroxyl; ii) $C_1$-$C_4$ alkoxy; iii) acylamino; iv) amino optionally substituted with one or two $C_1$-$C_4$ alkyl radicals, which may be identical or different, said alkyl radicals possibly forming, with the nitrogen atom which bears them, a heterocycle comprising from 5 to 7 members, optionally comprising another heteroatom which may or may not be different from nitrogen; v) or a quaternary ammonium group —$N^+R'R''R'''$, $M^-$ for which R', R'', R''', which may be identical or different, represent a hydrogen atom or a $C_1$-$C_4$ alkyl group, or else —$N^+R'R''R'''$ forms a heteroaryl such as imidazolium optionally substituted with a $C_1$-$C_4$ alkyl group, and $M^-$ represents the counterion of the corresponding organic acid, mineral acid or halide.

For the purpose of the present disclosure, and unless otherwise indicated, an "alkoxy radical" is an alkyloxy or alkyl-O-radical wherein the alkyl radical is a linear or branched, $C_1$-$C_{16}$ hydrocarbon-based radical, such as a $C_1$-$C_8$, hydrocarbon-based radical.

For the purpose of the present disclosure, and unless otherwise indicated, an "alkylthio radical" is an alkyl-S— radical wherein the alkyl radical is a linear or branched, $C_1$-$C_{16}$ hydrocarbon-based radical, such as a $C_1$-$C_8$, hydrocarbon-based radical. When the alkylthio group is optionally substituted, this implies that the alkyl group is optionally substituted as defined above.

For the purpose of the present disclosure, and unless otherwise indicated, an "organic or mineral acid salt" is for example chosen from a salt derived: i) from hydrochloric acid HCl; ii) from hydrobromic acid HBr; iii) from sulfuric acid $H_2SO_4$; iv) from alkylsulfonic acids: Alk-$S(O)_2OH$ such as methylsulfonic acid and ethylsulfonic acid; v) from arylsulfonic acids: Ar—$S(O)_2OH$ such as from benzenesulfonic acid and from toluenesulfonic acid; vi) from citric acid; vii) from succinic acid; viii) from tartaric acid; ix) from lactic acid; x) from alkoxysulfinic acids: Alk-O—S(O)OH such as from methoxysulfinic acid and from ethoxysulfinic acid; xi) from aryloxysulfinic acids such as from tolueneoxysulfinic acid and from phenoxysulfinic acid; xii) from phosphoric acid $H_3PO_4$; xiii) from acetic acid $CH_3COOH$; xiv) from triflic acid $CF_3SO_3H$ and xv) from tetrafluoroboric acid $HBF_4$.

For the purpose of the present disclosure, and unless otherwise indicated, an "anionic counterion" comprises an anion or an anionic group associated with the cationic charge of the dye; for example, the anionic counterion is chosen from: i) halides such as chloride or bromide; ii) nitrates; iii) sulfonates, among which are $C_1$-$C_6$ alkyl sulfonates: Alk-$S(O)_2$ $O^-$ such as methyl sulfonate or mesylate and ethyl sulfonate; iv) aryl sulfonates: Ar—$S(O)_2O^-$ such as benzene sulfonate and toluenesulfonate or tosylate; v) citrate; vi) succinate; vii) tartrate; viii) lactate; ix) alkyl sulfates: Alk-O—$S(O)O^-$ such as methyl sulfate and ethyl sulfate; x) arylsulfates: Ar—O—$S(O)O^-$ such as benzenesulfate and toluenesulfate; xi) alkoxysulfates: Alk-O—$S(O)_2O^-$ such as methoxy sulfate and ethoxy sulfate; xii) aryloxysulfates: Ar—O—$S(O)_2O^-$; xiii) phosphate; xiv) acetate; xv) triflate; and xvi) borates such as tetrafluoroborate.

For the purpose of the present disclosure, and unless otherwise indicated, the "solvates" comprise the hydrates and also the association with linear or branched $C_1$-$C_4$ alcohols such as ethanol, isopropanol or n-propanol.

One of the subjects of the present disclosure relates to thiol/disulfide fluorescent dyes of formula (I).

The thiol/disulfide fluorescent dyes of formula (I) are compounds capable of absorbing in the UV radiation or visible range at a wavelength $\gamma_{abs}$ ranging from 250 to 800 nm and capable of re-emitting in the visible range at an emission wavelength $\gamma_{em}$ ranging from 400 to 800 nm.

For example, the fluorescent compounds of formula (I) disclosed herein are dyes capable of absorbing in the visible range $\gamma_{abs}$ ranging from 400 to 800 nm and of re-emitting in the visible range $\gamma_{em}$ ranging from 400 to 800 nm. For example, the dyes of formula (I) are dyes capable of absorbing at a $\gamma_{abs}$ ranging from 420 to 550 nm and of re-emitting in the visible range at a $\gamma_{em}$ ranging from 470 to 600 nm.

The thiol fluorescent compounds disclosed herein of formula (I) for which m and n are 1 comprise an SY function which may be in the covalent form —S—Y or ionic form —$S^-Y^+$ depending on the nature of Y and on the pH of the medium.

When the compounds disclosed herein comprise several anionic counterions $An^-$, said counterions may be identical or different.

According to one embodiment, in the thiol fluorescent dyes of formula (I), m and n are 1 comprising an SY function, where Y comprises a hydrogen atom or an alkali metal. For example, Y represents a hydrogen atom.

According to another embodiment in the abovementioned formula (I), Y is a protecting group known to those skilled in the art, for instance those described in the books "*Protective Groups in Organic Synthesis*", T. W. Greene, John Wiley & Sons Ed., NY, 1981, pp. 193-217; "*Protecting Groups*", P. Kocienski, Thieme, 3rd Ed., 2005, Chap. 5. It being understood that Y as protective group cannot constitute with the sulphur atom on which it is linked a disulfide dye, i.e., it cannot constitute a formula (I) wherein m=2 and n=0. Y as the protective group cannot represent a group directly linked to the sulphur atom of formula (I) via another non oxidized sulphur atom.

For example, when Y represents a thiol-function-protecting group, Y is chosen from the following radicals:
($C_1$-$C_4$)alkylcarbonyl;
($C_1$-$C_4$)alkylthiocarbonyl;
($C_1$-$C_4$)alkoxycarbonyl;
($C_1$-$C_4$)alkoxythiocarbonyl;
($C_1$-$C_4$)alkylthiothiocarbonyl;
(di)($C_1$-$C_4$)(alkyl)aminocarbonyl;
(di)($C_1$-$C_4$)(alkyl)aminothiocarbonyl;
arylcarbonyl such as phenylcarbonyl;
aryloxycarbonyl;
aryl($C_1$-$C_4$)alkoxycarbonyl;
(di)($C_1$-$C_4$)(alkyl)aminocarbonyl such as dimethylaminocarbonyl;
($C_1$-$C_4$)(alkyl)arylaminocarbonyl;
$SO_3^-$, $M^+$ with $M^+$ representing an alkali metal such as sodium or potassium, or else $An^-$ of formula (I) and $M^+$ are absent;
optionally substituted aryl such as phenyl, dibenzosuberyl or 1,3,5-cycloheptatrienyl, optionally substituted heteroaryl; including for example the cationic or noncationic heteroaryl comprising from 1 to 4 heteroatoms below:

i) monocyclic comprising 5, 6 or 7 members, such as furanyl or furyl, pyrrolyl or pyrryl, thiophenyl or thienyl, pyrazolyl, oxazolyl, oxazolium, isoxazolyl, isoxazolium, thiazolyl, thiazolium, isothiazolyl, isothiazolium, 1,2,4-triazolyl, 1,2,4-triazolium, 1,2,3-triazolyl, 1,2,3-triazolium, 1,2,4-oxazolyl, 1,2,4-oxazolium, 1,2,4-thiadiazolyl, 1,2,4-thiadiazolium, pyrylium, thiopyridyl, pyridinium, pyrimidinyl, pyrimidinium, pyrazinyl, pyrazinium, pyridazinyl, pyridazinium, triazinyl, triazinium, tetrazinyl, tetrazinium, azepine, azepinium, oxazepinyl, oxazepinium, thiepinyl, thiepinium, imidazolyl, imidazolium;

ii) bicyclic comprising 8 to 11 members, such as indolyl, indolinium, benzoimidazolyl, benzoimidazolium, benzoxazolyl, benzoxazolium, dihydrobenzoxazolinyl, benzothiazolyl, benzothiazolium, pyridoimidazolyl, pyridoimidazolium, thienocycloheptadienyl, these monocyclic or bicyclic groups being optionally substituted with one or more groups such as $(C_1-C_4)$alkyl, for instance methyl, or polyhalo$(C_1-C_4)$ alkyl, for instance trifluoromethyl;

iii) or tricyclic ABC below:

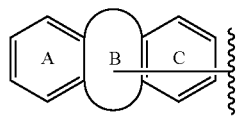

wherein the two rings A, C optionally comprise a heteroatom, and the ring B comprises a 5-, 6- or 7-membered, such as a 6-membered ring, and comprises at least one heteroatom, for instance piperidyl or pyranyl;

optionally cationic, optionally substituted heterocycloalkyl, the heterocycloalkyl group is chosen from for example a saturated or partially saturated, 5-, 6- or 7-membered monocyclic group comprising from 1 to 4 heteroatoms chosen from oxygen, sulfur and nitrogen, such as di/tetrahydrofuranyl, di/tetrahydrothiophenyl, di/tetrahydropyrrolyl, di/tetrahydropyranyl, di/tetra-hexahydrothiopyranyl, dihydropyridyl, piperazinyl, piperidinyl, tetramethylpiperidinyl, morpholinyl, di/tetra/hexahydroazepinyl or di/tetrahydropyrimidinyl, these groups being optionally substituted with one or more groups such as $(C_1-C_4)$ alkyl, oxo or thioxo; or the heterocycle comprises the following group:

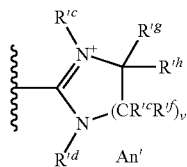

in which $R'^c$, $R'^d$, $R'^e$, $R'^f$, $R'^g$ and $R'^h$, which may be identical or different, are chosen from a hydrogen atom or a $(C_1-C_4)$ alkyl group, or else two groups $R'^g$ with $R'^h$, and/or $R'^e$ with $R'^f$, form an oxo or thioxo group, or else $R'^g$ with $R'^e$ together form a cycloalkyl; and v is chosen from an integer ranging from 1 to 3; for example, $R'^c$ to $R'^h$ represent a hydrogen atom; and $An'^-$ represents a counterion;

isothiouronium;

—$C(NR'^cR'^d)=N^+R'^eR'^f$; $An^-$ with $R'^c$, $R'^d$, $R'^e$ and $R'^f$, which may be identical or different, are chosen from a hydrogen atom or a $(C_1-C_4)$alkyl group; for example, $R'^c$ to $R'^f$ represent a hydrogen atom; and $An'^-$ represents a counterion;

isothiourea;

—$C(NR'^cR'^d)=NR'^e$; $An^-$ with $R'^c$, $R'^d$, $R'^e$ and $An^-$ as defined above;

optionally substituted (di)aryl$(C_1-C_4)$alkyl, such as 9-anthracenylmethyl, phenylmethyl or diphenylmethyl optionally substituted with one or more groups for example chosen from $(C_1-C_4)$ alkyl, $(C_1-C_4)$ alkoxy such as methoxy, hydroxyl, alkylcarbonyl and (di)$(C_1-C_4)$(alkyl)amino such as dimethylamino;

optionally substituted (di)heteroaryl$(C_1-C_4)$alkyl, the heteroaryl group is for example cationic or noncationic, and monocyclic, comprising 5 or 6 members and from 1 to 4 heteroatoms chosen from nitrogen, oxygen and sulfur, such as the groups pyrrolyl, furanyl, thiophenyl, pyridyl, pyridyl N-oxide such as 4-pyridyl or 2-pyridyl N-oxide, pyrylium, pyridinium or triazinyl, optionally substituted with one or more groups such as alkyl, such as methyl, for example the (di)heteroaryl$(C_1-C_4)$alkyl is (di)heteroarylmethyl or (di)heteroarylethyl;

$CR^1R^2R^3$ with $R^1$, $R^2$ and $R^3$, which may be identical or different, are chosen from a halogen atom or a group chosen from:

i) $(C_1-C_4)$alkyl;

ii) $(C_1-C_4)$alkoxy;

iii) optionally substituted aryl, such as phenyl optionally substituted with one or more groups such as $(C_1-C_4)$alkyl, $(C_1-C_4)$alkoxy or hydroxyl; or iv) optionally substituted heteroaryl, such as thiophenyl, furanyl, pyrrolyl, pyranyl or pyridyl, optionally substituted with a $(C_1-C_4)$alkyl group;

v) $P(Z^1)R'^1R'^2R'^3$ with $R'^1$ and $R'^2$, which may be identical or different, comprising a hydroxyl, $(C_1-C_4)$alkoxy or alkyl group, $R'^3$ comprising a hydroxyl or $(C_1-C_4)$alkoxy group and $Z^1$ comprising an oxygen or sulfur atom;

a sterically hindered cyclic; and optionally substituted alkoxyalkyl, such as methoxymethyl (MOM), ethoxyethyl (EOM) or isobutoxymethyl.

According to another embodiment, the protected thiol fluorescent dyes of formula (I) for which m and n are 1 comprise a group Y i) which is a cationic, aromatic 5- or 6-membered monocyclic heteroaryl group comprising from 1 to 4 heteroatoms chosen from oxygen, sulfur and nitrogen, such as oxazolium, isoxazolium, thiazolium, isothiazolium, 1,2,4-triazolium, 1,2,3-triazolium, 1,2,4-oxazolium, 1,2,4-thiadiazolium, pyrylium, pyridinium, pyrimidinium, pyrazinyl, pyrazinium, pyridazinium, triazinium, tetrazinium, oxazepinium, thiepinyl, thiepinium or imidazolium; ii) cationic 8- to 11-membered bicyclic heteroaryl group, such as indolinium, benzoimidazolium, benzoxazolium or benzothiazolium, these monocyclic or bicyclic heteroaryl groups being optionally substituted with one or more groups such as alkyl, for instance methyl, or polyhalo$(C_1-C_4)$alkyl, for instance trifluoromethyl; iii) or heterocyclic group below:

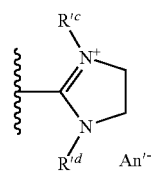

wherein R'$^c$ and R'$^d$, which may be identical or different, are chosen from a hydrogen atom or a (C$_1$-C$_4$)alkyl group; for example, R'$^c$ to R'$^d$ are chosen from a (C$_1$-C$_4$)alkyl group such as methyl; and An'$^-$ represents an anionic counterion.

For example, Y is chosen from a group chosen from oxazolium, isoxazolium, thiazolium, isothiazolium, 1,2,4-triazolium, 1,2,3-triazolium, 1,2,4-oxazolium, 1,2,4-thiadiazolium, pyrylium, pyridinium, pyrimidinium, pyrazinium, pyridazinium, triazinium and imidazolium, benzoimidazolium, benzoxazolium, benzothiazolium, these groups being optionally substituted with one or more (C$_1$-C$_4$)alkyl groups, for example methyl.

For example, Y comprises an alkali metal or a protecting group such as:

(C$_1$-C$_4$)alkylcarbonyl, such as methylcarbonyl or ethylcarbonyl;

arylcarbonyl such as phenylcarbonyl;

(C$_1$-C$_4$)alkoxycarbonyl;

aryloxycarbonyl;

aryl(C$_1$-C$_4$)alkoxycarbonyl;

(di)(C$_1$-C$_4$)(alkyl)aminocarbonyl such as dimethylaminocarbonyl;

(C$_1$-C$_4$)(alkyl)arylaminocarbonyl;

optionally substituted aryl, such as phenyl;

5- or 6-membered monocyclic heteroaryl, such as imidazolyl or pyridyl;

5- or 6-membered cationic monocyclic heteroaryl, such as pyrylium, pyridinium, pyrimidinium, pyrazinium, pyridazinium, triazinium or imidazolium; these groups being optionally substituted with one or more identical or different (C$_1$-C$_4$)alkyl groups, such as methyl;

8- to 11-membered cationic bicyclic heteroaryl, such as benzoimidazolium or benzoxazolium; these groups being optionally substituted with at least one identical or different (C$_1$-C$_4$)alkyl group, such as methyl;

cationic heterocycle of the following formula:

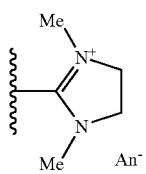

isothiouronium —C(NH$_2$)=N$^+$H$_2$; An$^-$;

isothiourea —C(NH$_2$)=NH; and

SO$_3^-$, M$^+$ with M$^+$ comprising an alkali metal such as sodium or potassium, or else An$^-$ of formula (I) and M$^+$ are absent.

According to one embodiment, the disulfide fluorescent dyes of formula (I) when n is 2 and m is 0 have a C2 axis of symmetry between the two sulfur atoms of the central disulfide radical.

According to another embodiment, the dyes of the disclosure belong to one of the two formulae (Ia) and (Ib) below:

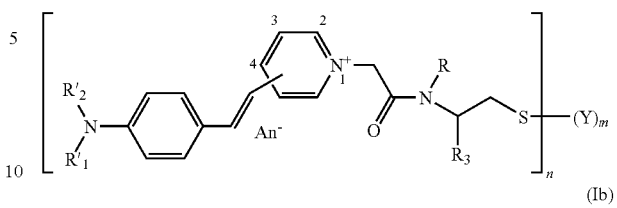

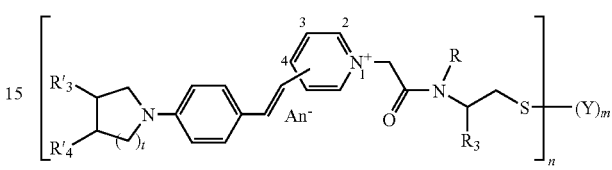

the organic or mineral acid salts, optical isomers and geometric isomers thereof and the solvates such as hydrates;

in which formulae (Ia) and (Ib):

R'$_1$ is chosen from a C$_1$-C$_4$ alkyl group substituted with at least one hydroxyl group, such as a single hydroxyl group; or —C(O)—O$^-$;

R'$_2$ are chosen from a C$_1$-C$_4$ alkyl group optionally substituted with at least one hydroxyl group R'$_3$ and R'$_4$, which may be identical or different, are chosen from a hydrogen atom, a hydroxyl group, a hydroxy(C$_1$-C$_4$) alkyl group or a —C(O)OR' group, with R' chosen from a hydrogen atom or a C$_1$-C$_4$ alkyl group, or else a —C(O)—O$^-$ group and, in this case, an anionic counterion An$^-$ is absent, wherein only one of these two radicals R'$_3$ or R'$_4$ can represent a hydrogen atom;

R$_3$ is chosen from a hydrogen atom or a —C(O)OR" group with R" chosen from a hydrogen atom or a C$_1$-C$_4$ alkyl group, or else R$_3$ represents a —C(O)—O$^-$ group and, in this case, an anionic counterion An$^-$ is absent;

n is an integer ranging from 1 to 2;

m is an integer ranging from 0 to 1;

t is an integer ranging from 1 to 2;

An$^-$ represents an anionic counterion;

Y is chosen from: i) a hydrogen atom; ii) an alkali metal; iii) an alkaline earth metal; iv) an ammonium group: N$^+$R$^\alpha$R$^\beta$R$^\gamma$R$^\delta$, An$^-$ or a phosphonium group: P$^+$R$^\alpha$R$^\beta$R$^\gamma$R$^\delta$, An$^-$ with R$^\alpha$, R$^\beta$, R$^\gamma$ and R$^\delta$, which may be identical or different, are chosen from a hydrogen atom or a (C$_1$-C$_4$)alkyl group, and An$^-$ as defined above; or v) a thiol-function-protecting group;

wherein:

the bond between the pyridinium ring and the double bond of the styryl group is positioned in the 2- or 4-position with respect to the pyridinium;

when n=1, m=1, then Y=H or a thiol-function-protecting group and when n=2, then m=0.

In certain of these embodiments, when R'$_1$ is a —C(O)—O$^-$ group, an anionic counterion An$^-$ is absent.

In certain of these embodiments, R'$_2$ is chosen from a C$_1$-C$_4$ alkyl group optionally substituted with one or more hydroxyl groups, such as a single hydroxyl group. In certain embodiments, R'$_1$ and R'$_2$ are identical.

In another embodiments R'$_2$ is chosen from a C$_1$-C$_4$ alkyl group, which is optionally substituted, and R'$_1$ represent a C$_1$-C$_4$ alkyl group substituted by an hydroxyl or a carboxylate group —C(O)O$^-$. In certain embodiments, R'$_2$ is chosen from a C$_1$-C$_4$ alkyl group, which is not substituted.

By way of example, mention may be made of the following fluorescent dyes belonging to formula (I), (Ia) or (Ib):

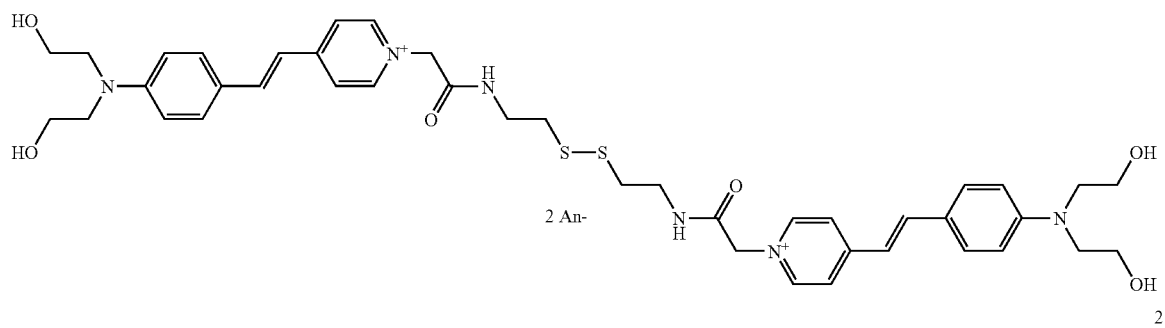
1
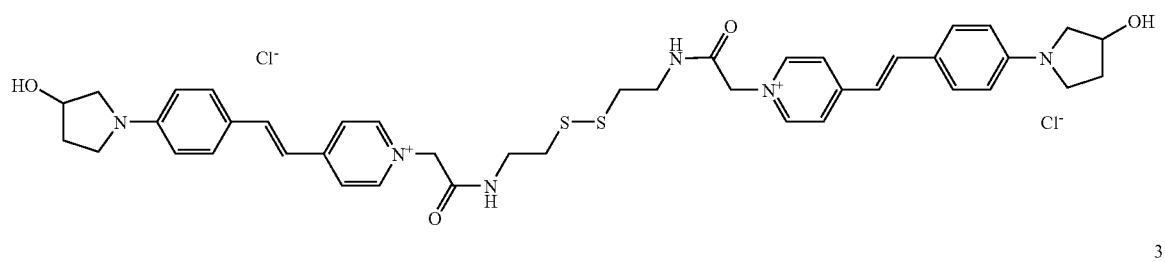
2
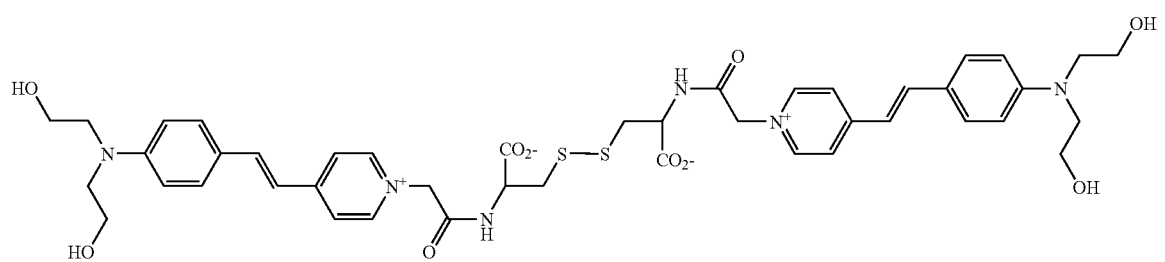
3
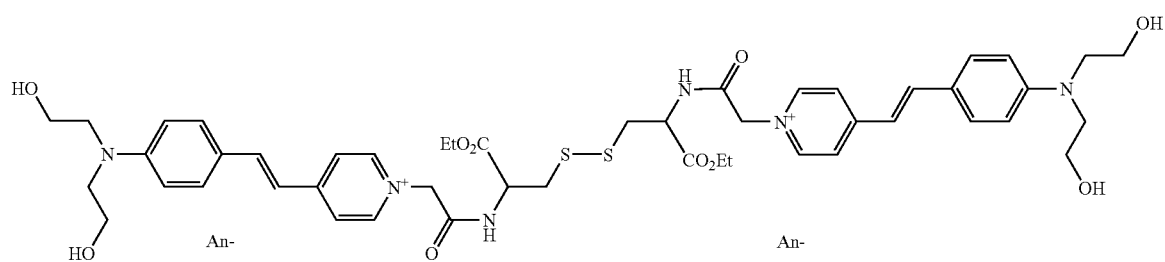
4
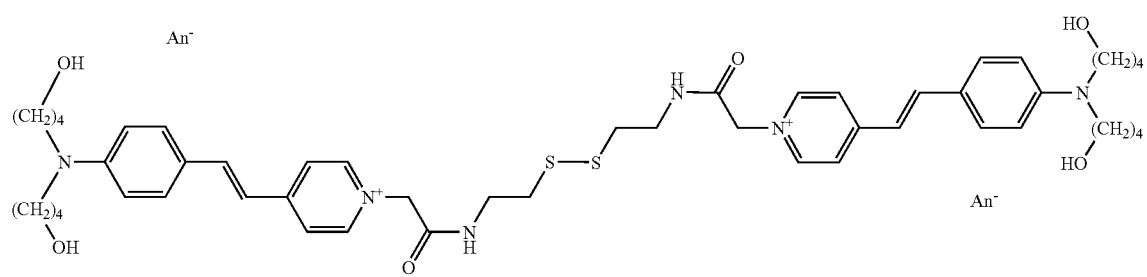
5

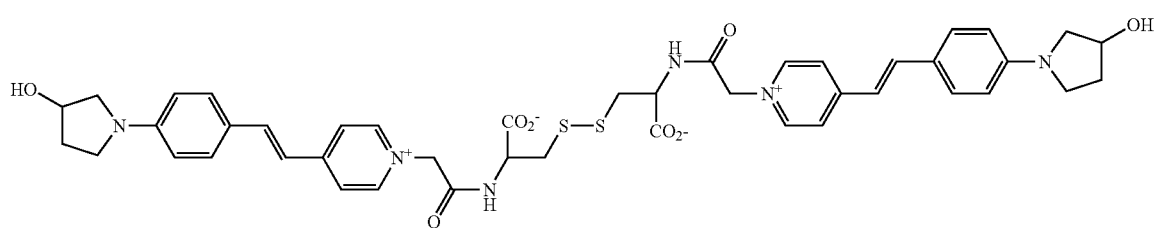
6
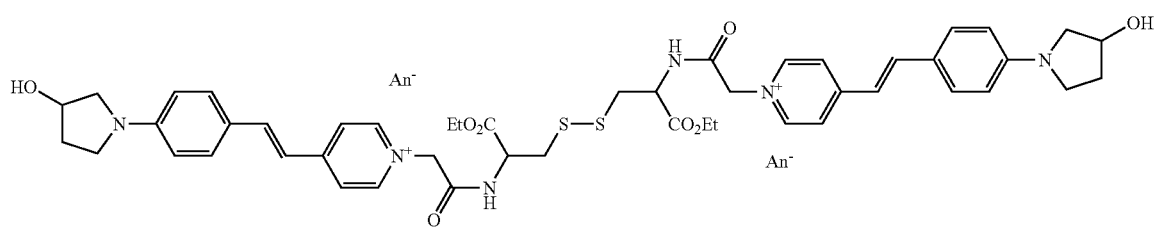
7
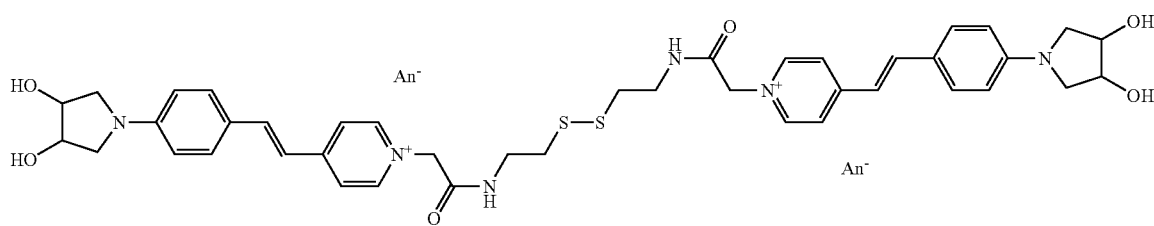
8
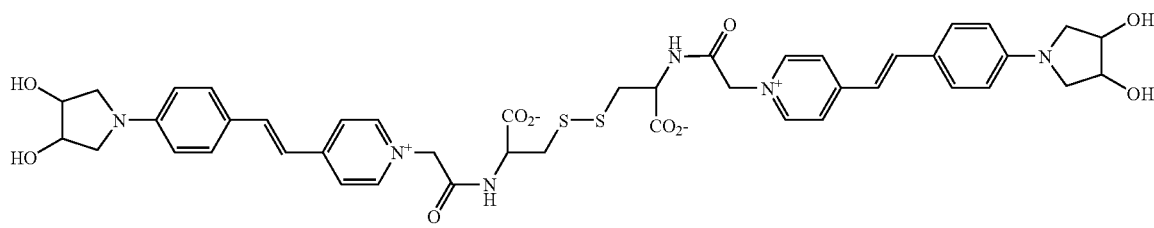
9
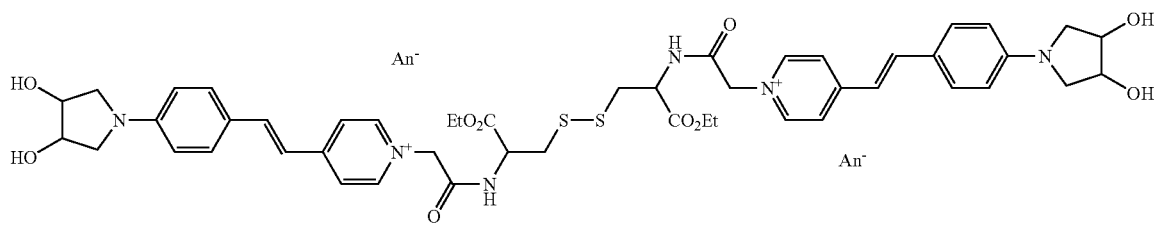
10
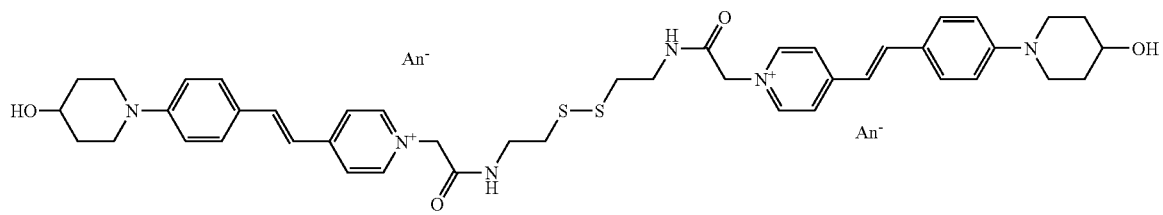
11

-continued
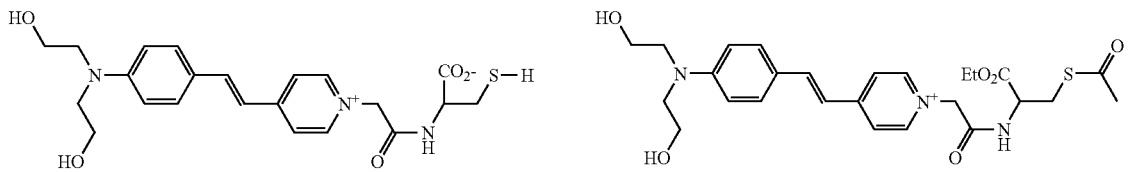
12
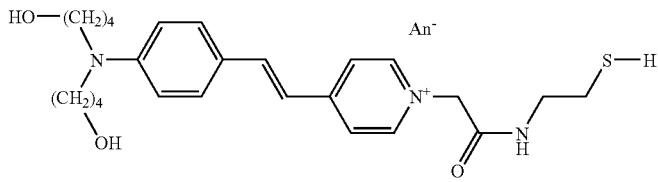
13
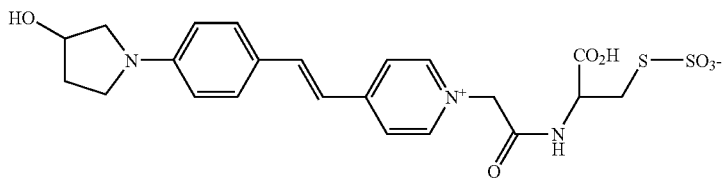
14
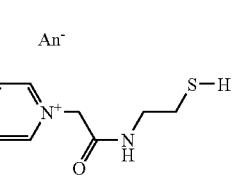
15
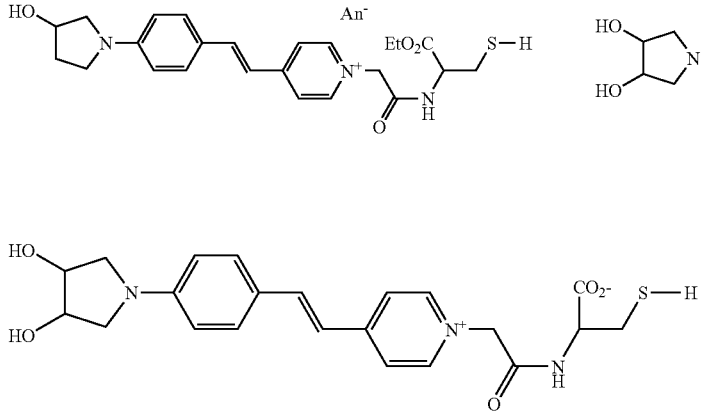
16
17
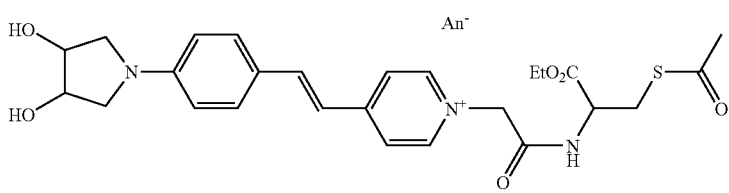
18
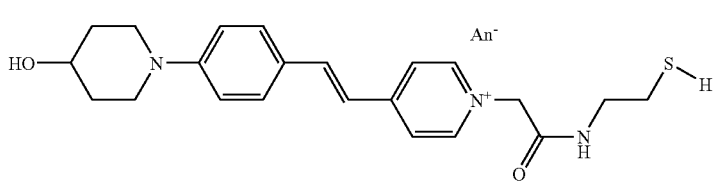
19
20

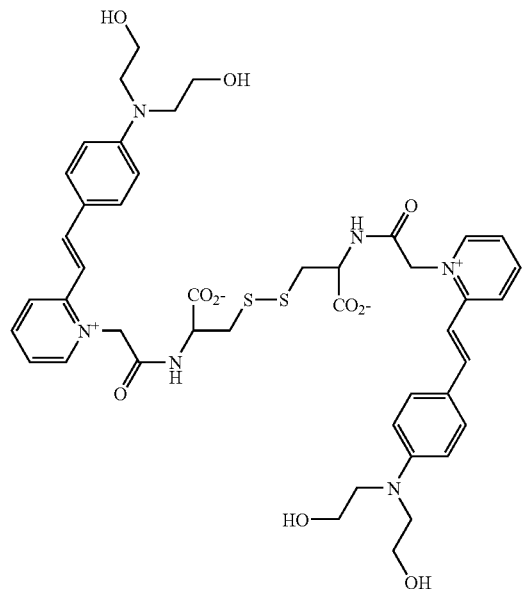
21
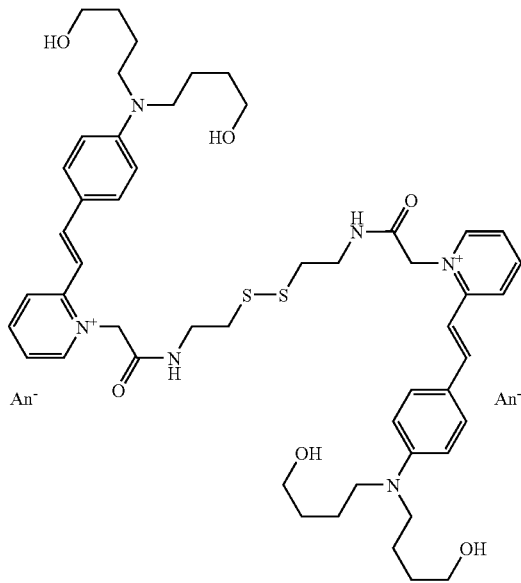
22
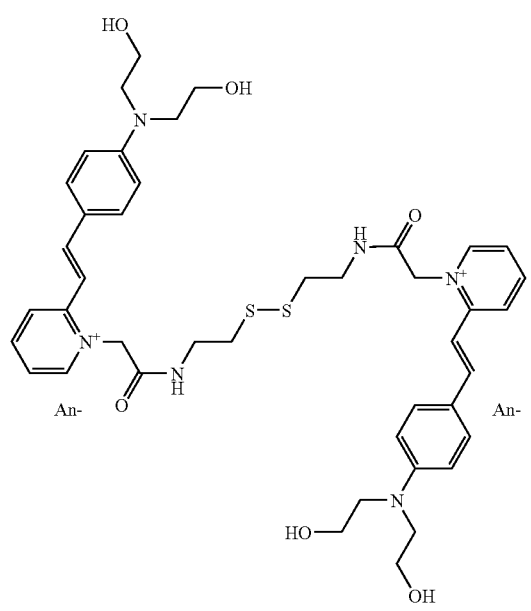
23
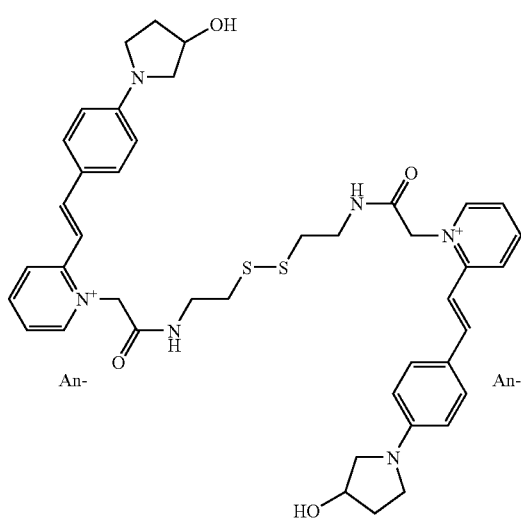
24

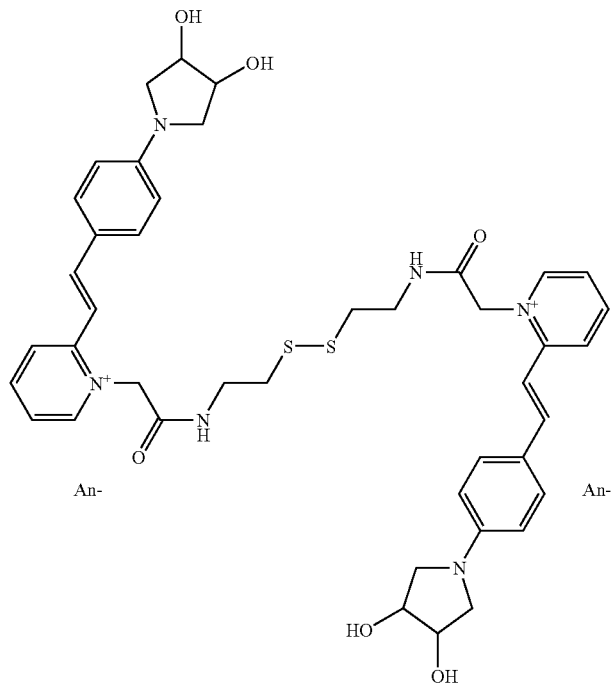
25
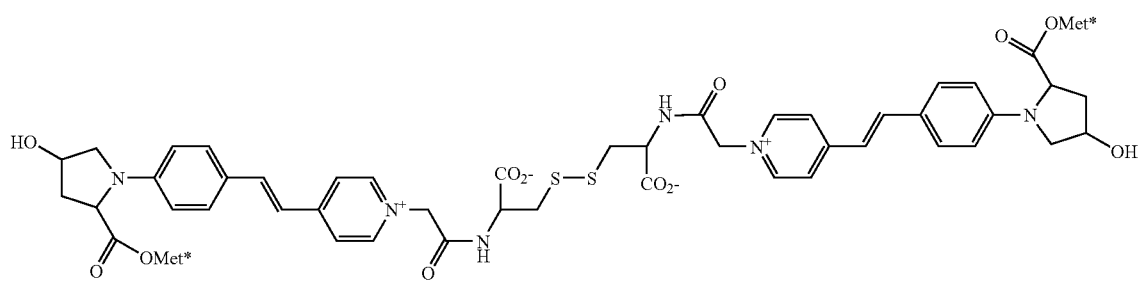
26
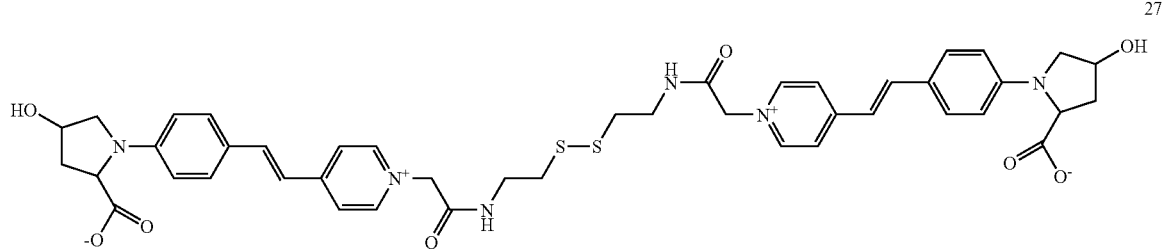
27

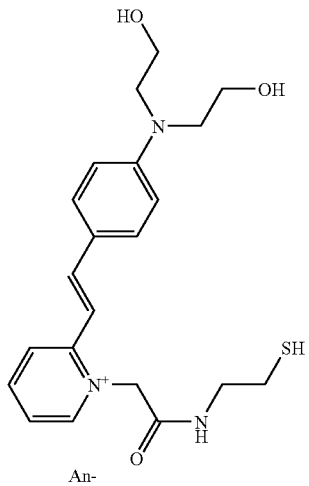
28
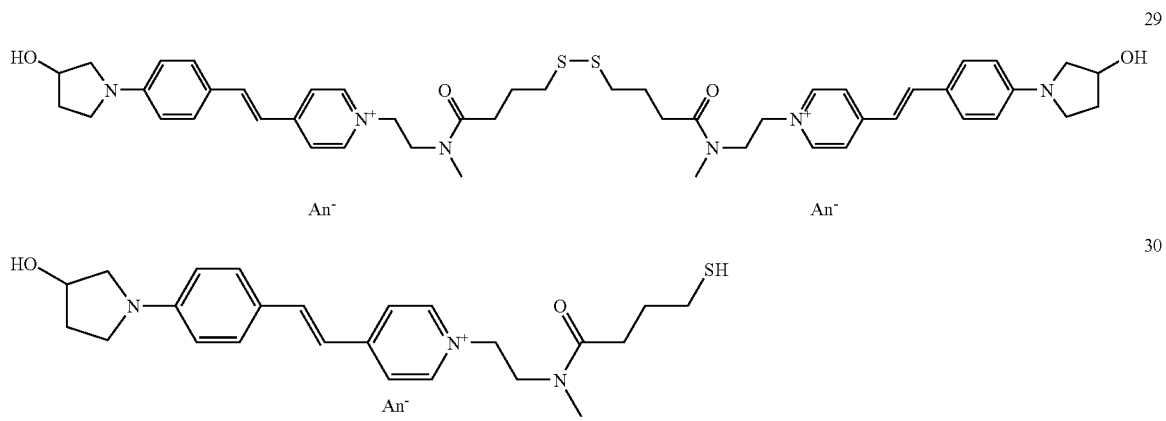
29
30
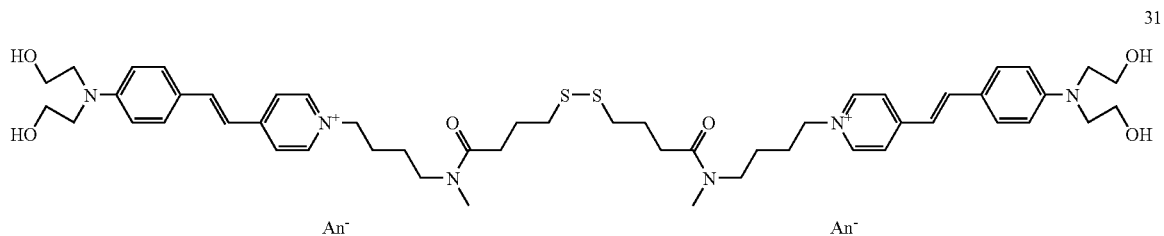
31
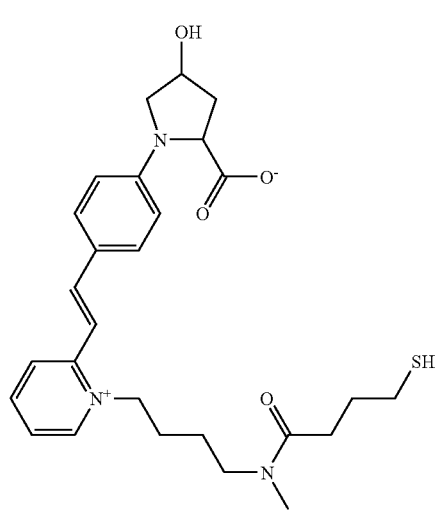
32

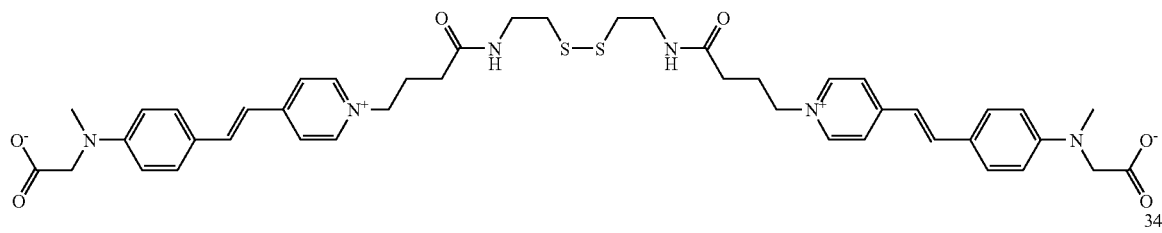

33

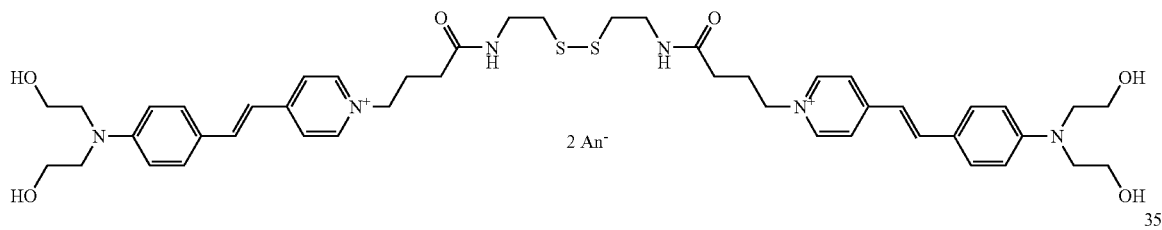

34

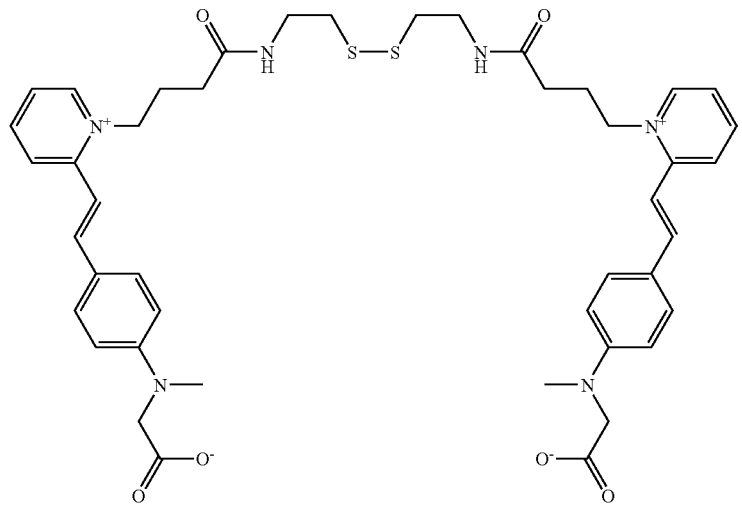

35

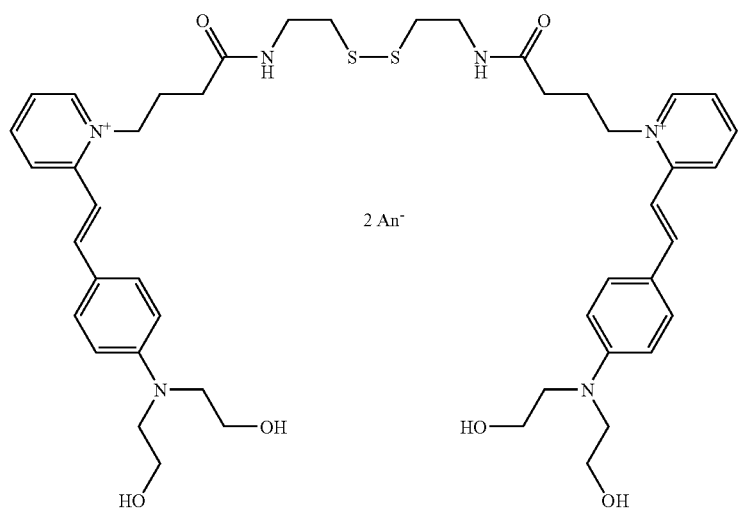

36 with An⁻ representing an anionic counterion.

To prepare the thiol/disulfide fluorescent dyes disclosed herein, mention may be made of the following general pathways.

The protected thiol dyes of formula (II') can be synthesized in two stages The first stage comprises preparing the nonprotected thiol dye (II") according to the methods known to those skilled in the art, for instance *"Thiols and organic sulfides"*, "Thiocyanates and isothiocyanates, organic", Ullmann's Encyclopedia, Wiley-VCH, Weinheim, 2005. In addition, the second step comprises protecting the thiol function according The thiol compound (II″) may also be metallated with an alkali metal or alkaline earth metal Met* so as to produce the thiolate fluorescent dye of formula (II‴).

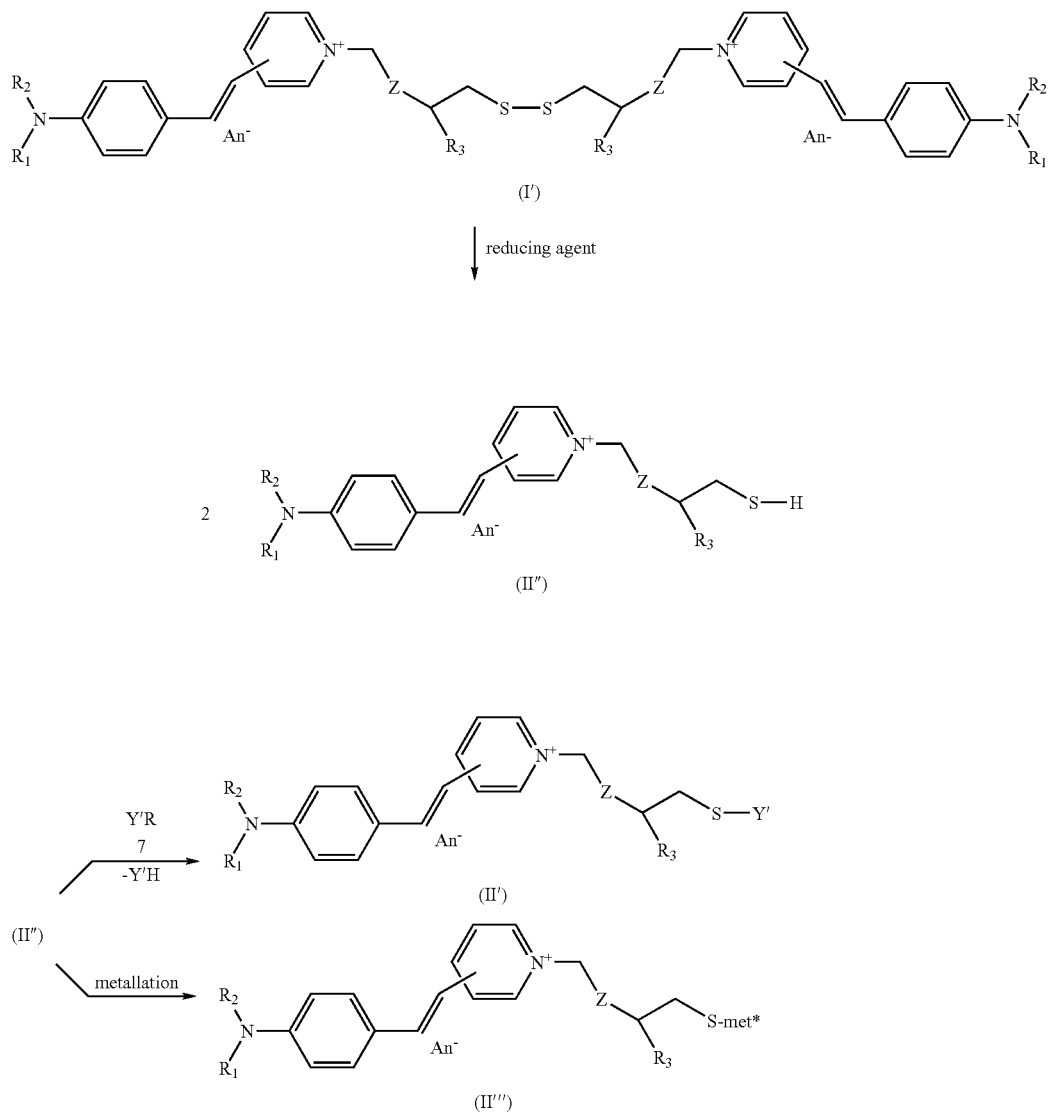

to the conventional methods known to those skilled in the art in order to produce the protected thiol dyes of formula (II′). By way of example, for protecting the thiol function —SH of the thiol dye, use may be made of the methods in the books "*Protective Groups in Organic Synthesis*", T. W. Greene, John Willey & Sons Ed., NY, 1981, pp. 193-217; "*Protecting Groups*", P. Kocienski, Thieme, 3rd Ed., 2005, Chap. 5.

This method can be illustrated by means of the method comprising i) generating thiol fluorescent dyes of formula (II″) by reduction of a heterocyclic, two-chromophore fluorescent dye bearing a disulfide function —S—S— such as (I′) and ii) protecting said thiol function of (II″), according to the conventional methods, with the reactant 7 Y′R in order to obtain the protected thiol fluorescent dyes of formula (II′).

with Y′ representing a thiol-function-protecting group; Met* representing an alkali metal or an alkaline earth metal, such as sodium or potassium, it being understood that, when the metal is an alkaline earth metal, 2 chromophores comprising a thiolate —S⁻ function can be associated with 1 $Metal^{2+}$;

with $R_1 R_2$, $R_3$, $R_4$, m, n, G and An⁻ being as defined above; Y′ represents a thiol-function-protecting group; and R represents a nucleofuge leaving group, for instance mesylate, tosylate, triflate or halide.

According to another possibility, a protected thiol compound (b) protected with a protecting group Y′ as defined above, prepared according to one of the procedures described in the books described above, said protected thiol compound comprising at least one nucleophilic function, can be reacted with a sufficient, for example equimolar, amount of a "reactive fluorescent chromophore" or of a compound comprising such a "reactive fluorescent chromophore" (a). In other words, (a) comprises an electrophilic function so as to form a Σ covalent bond, as can be shown schematically below in the preparation of fluorescent dyes of formula (II'a) which are a subset of the fluorescent dyes (II'):

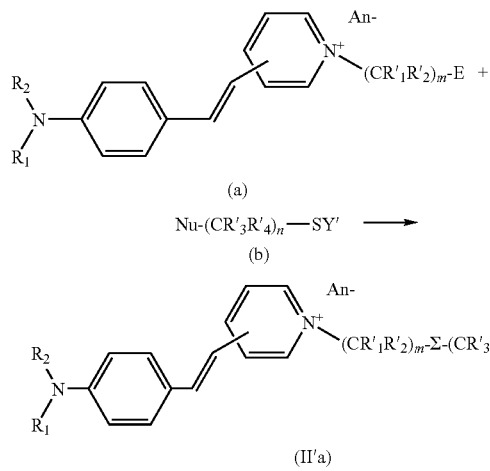

with $R_1$, $R_2$, Y' and An⁻ as defined above; $R'_1$, $R'_2$, $R'_3$, $R'_4$ are chosen from $C_1$-$C_4$ alkyl chains optionally substituted with a carboxylic acid group, a carboxylic acid salt, an ester function or a hydrogen group, m and n are integers ranging from 1 to 4, Nu representing a nucleophilic group of amine type; E representing an electrophilic group; and Σ the linking group generated after attack by the nucleophile on the electrophile.

By way of example, the Σ bonds that can be generated are listed in the table below based on condensation of electrophiles with nucleophiles:

| Electrophiles E | Nucleophiles Nu | Σ Covalent bonds |
|---|---|---|
| Activated esters* | Amines | Carboxamides |
| Acyl nitrides | Amines | Carboxamides |
| Acyl halides | Amines | Carboxamides |
| Acyl cyanides | Amines | Carboxamides |
| Anhydrides | Amines | Carboxamides |
| Carboxylic acids | Amines | Carboxamides | the activated esters of general formula —CO-Part with Part representing a leaving group such as oxysuccinimidyl, oxybenzotriazolyl, aryloxy which is optionally substituted;

It is also possible to use a thiol reactant (α): Y'—SH comprising a Y' group as defined above, the nucleophilic SH function of which can react with the carbon atom in the α-position with respect to the halogen atom borne by a fluorescent chromophore, so as to give the protected thiol fluorescent dye of formula (II'):

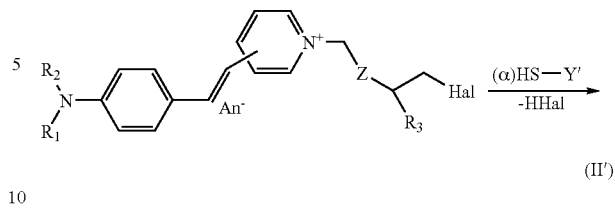

with $R_1$, $R_2$, $R_3$, Z, Y', (II') and An⁻ as defined above, and Hal representing a nucleofuge halogen atom such as bromine, iodine or chlorine.

For example, a nucleofuge leaving group may be replaced with a group derived from thiourea (S=C(NRR)NRR), or thiourea, so as to generate isothiouroniums. For example, if the thiourea group is a thioimidazolinium (β), the reaction scheme is the following:

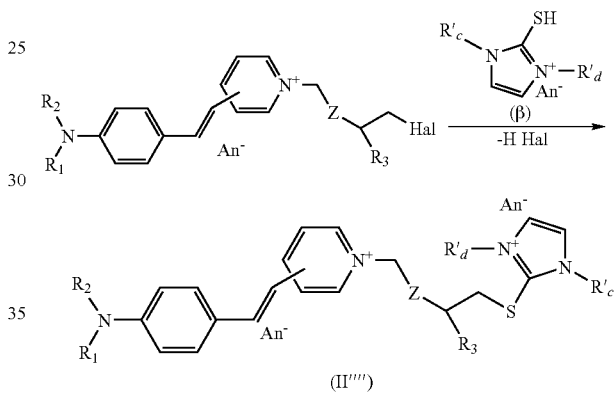

with $R_1$, $R_2$, $R_3$, Z, Hal and An as defined above, $R'_c$ and $R'_d$ are chosen from $C_1$-$C_4$ alkyl groups; (II'''') representing a dye which is a subset of formula (II').

Another variant may make it possible to obtain certain compounds (II') using cyclic thiourea of imidazoline type (b'), followed by alkylation of said imidazoline using $R'_d$-Lg, with Lg being a leaving group such as chloride, bromide, tosylate or mesylate:

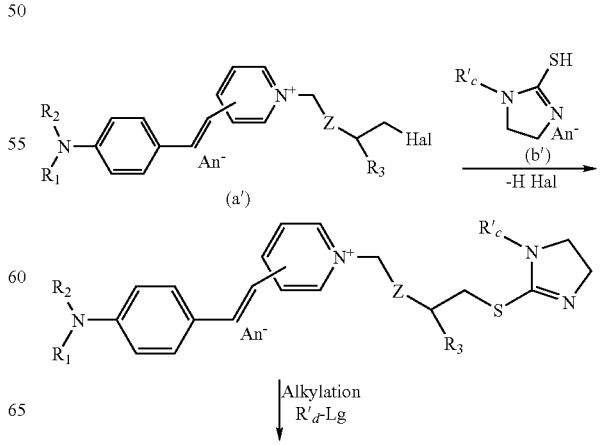

-continued

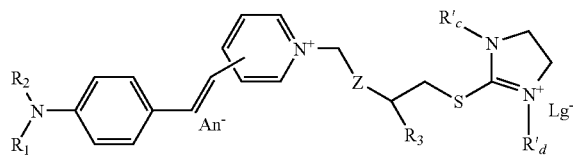

with $R_1$, $R_2$, $R_3$, Z, $R'_c$, $R'_d$, (II'), Hal and An− as defined above.

A variant is to use, in place of the halide comprising the fluorescent chromophore (a'), a chromophore comprising another type of nucleofuge such as tosylate or mesylate.

In accordance with another possibility, certain protected thiol fluorescent dyes (II'a) can be obtained by reacting a protected thiol compound with a compound bearing a carboxylic acid function that is activated, according to the conventional methods (for example, reaction with a carbodiimide or with thionyl chloride). The resulting product (d) is subsequently reacted with a fluorescent chromophore bearing a nucleophilic function (c) of primary or secondary amine type.

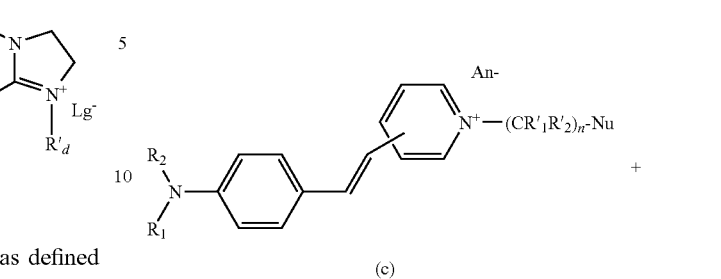

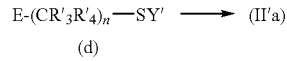

with $R_1$, $R_2$, $R'_c$, $R'_d$, An−, $R'_1$, $R'_2$, $R'_3$, $R'_4$, Y', m, n, E, Nu and (II'a) as defined above.

Another variant is to use a thiolactone derivative as represented by the scheme below:

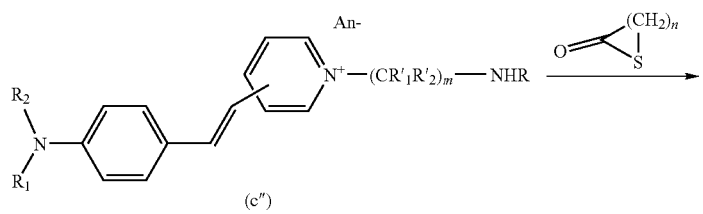

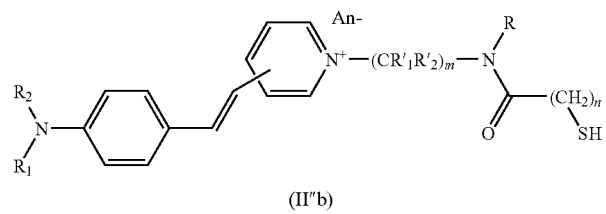

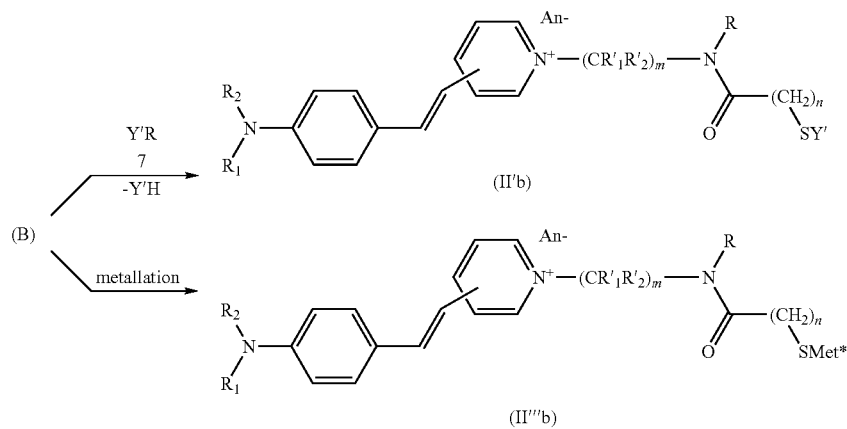

with $R_1$, $R_2$, $R'_1$, $R'_2$, Y', Met*, m, n and An⁻ as defined above. The thiolactone derivative is for example chosen with n=3.

One synthesis variant is to combine the above pathway with the first pathway, i.e., using two equivalents of the nucleophile reactant (c) with a dielectrophilic disulfide reactant (i), it is possible to generate, after condensation, the dichromophoric disulfide product (I), it being possible for the latter to undergo a reduction so as to form the heterocyclic fluorescent thiol dye (II″a) which, in turn, may be either protected so as to form the protected thiol fluorescent dye in (II″a) or metallated with an alkali metal so as to give the metallated heterocyclic thiol fluorescent dye (II‴a):

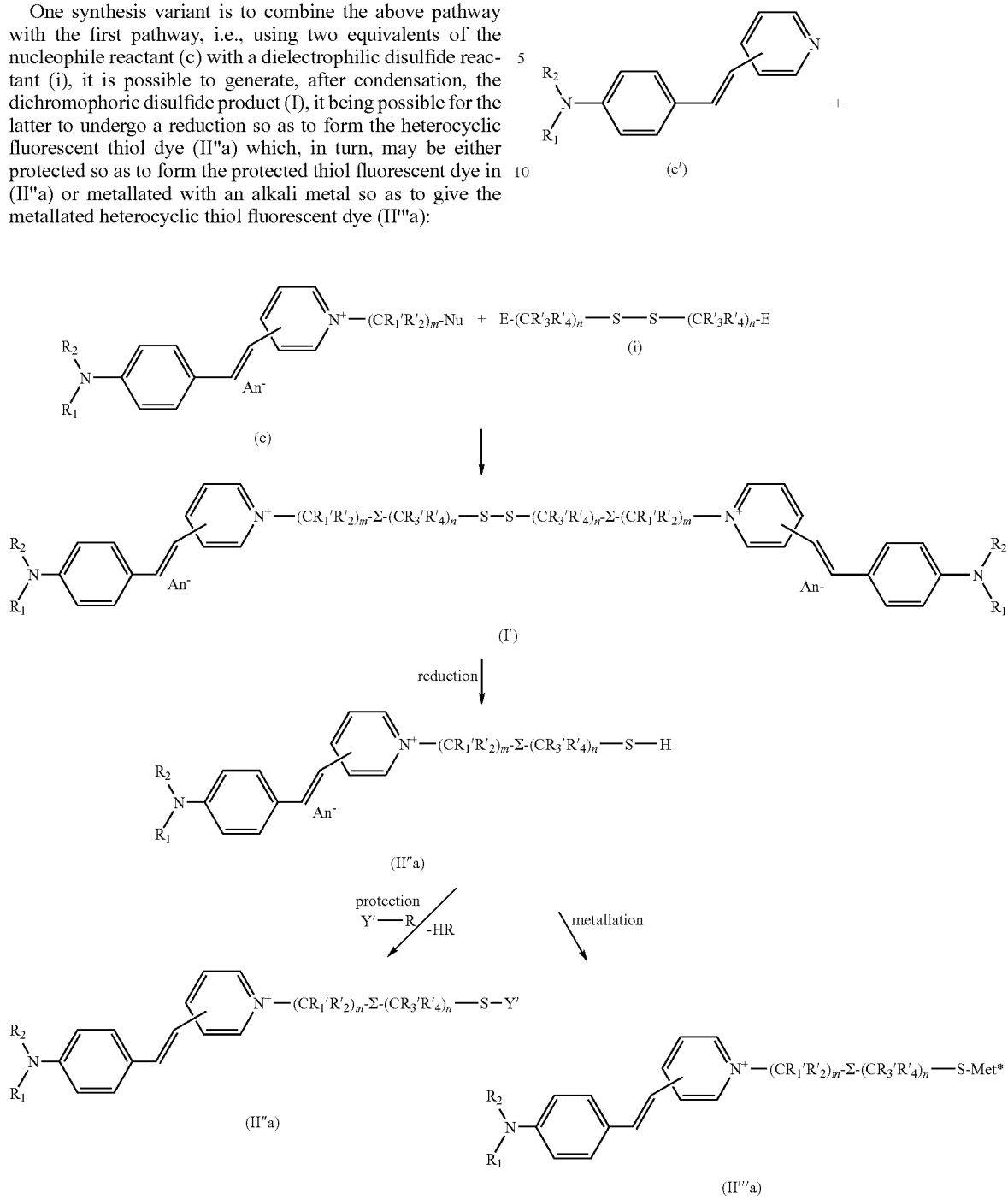

In accordance with another possibility, the protected thiol fluorescent dyes of formula (II') can be obtained by reaction of a compound d' comprising a thiol group protected with a Y' group, and a leaving group Lg, such as a halide group (chlorine, bromine) or a hydroxyl group activated beforehand to a nucleofuge leaving group (d'), for instance mesylate, tosylate, triflate or halide, with a styrylpyridine chromophore (c').

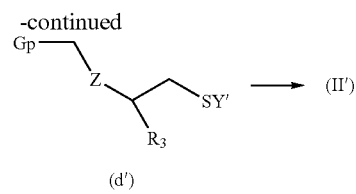

with $R_1$, $R_2$, $R_3$, Z, Y', and (II') as defined above.

In accordance with another possibility, the thiol fluorescent dyes of formula (I) disclosed herein can be obtained by reaction of a compound comprising a thiol group protected by a group Y as defined above and an electrophilic group (f), with a pyridinium compound comprising a nucleophilic group. By way of example, an aldehyde or a thioaldehyde when G' represents an oxygen atom or a sulfur may be condensed with an "activated methylene" such as alkylpyridinium (e) so as to generate an ethylene bond >C=C<. This reaction is commonly known as "Knoevenagel" condensation. The term "activated methylenes" is intended to imply those which comprise, in the 2- or 4-position with respect to the pyridinium group, a methylene group $CH_3$—:

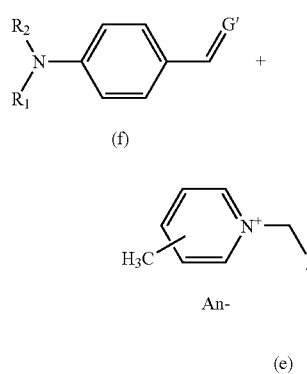

with $R_1$, $R_2$, $R_3$, Z, Y' and $An^-$ as defined above and G comprising an oxygen or sulfur atom.

Reference may be made to the book *Advanced Organic Chemistry*, "Reactions, Mechanisms and Structures", J. March, 4th Ed., John Willey & Sons, 1992 or T. W. Greene "*Protective Groups in Organic Synthesis*", for further details on the operating conditions used for the processes mentioned above.

The thiol fluorescent dyes formed can be converted to —SY' protected thiol fluorescent dyes by protection of the —SH thiol using the conventional protecting groups. The thiol fluorescent dyes are metallated by also using the conventional methods known to those skilled in the art, such as those described in *Advanced Organic Chemistry*, "Reactions, Mechanisms and Structures", J. March, 4th Ed., John Willey & Sons, NY, 1992.

The protected thiol dyes can be deprotected by conventional pathways such as those described in the books "*Protective Groups in Organic Synthesis*", T. W. Greene, John Willey & Sons Ed., NY, 1981; "*Protecting Groups*", P. Kocienski, Thieme, 3rd Ed., 2005.

The starting reactants are commercially available or accessible by conventional methods known to those skilled in the art. By way of example, it is possible to synthesize the reactant (I') using two equivalents of pyridine derivative 1 and one equivalent of disulfide reactant comprising two leaving groups Lg, so as to give the dipyridinium disulfide salt 3 which can, in turn, condense with two equivalents of aryl compound comprising an aldehyde/thioaldehyde group 4, so as to give 5.

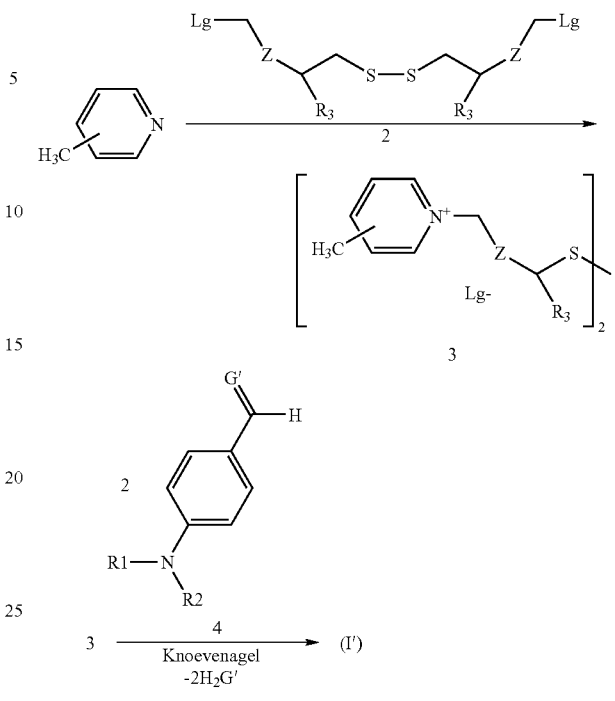

with Lg representing a nucleofuge leaving group, for instance mesylate, tosylate, triflate or halide. The counterions $Lg^-$ of the compounds (I') above can be replaced with counterions $An^-$ of other natures using methods known to those skilled in the art, in particular by ion-exchange resin.

Reference may be made to the book *Advanced Organic Chemistry*, "Reactions, Mechanisms and Structures", J. March, 4th Ed., John Willey & Sons, 1992 or T. W. Greene "*Protective Groups in Organic Synthesis*", for further details on the operating conditions used for the processes mentioned above.

The thiol fluorescent dyes formed can be converted to —SY' protected thiol fluorescent dyes by protection of the —SH thiol using the conventional protecting groups. The thiol fluorescent dyes are metallated by also using the conventional methods known to those skilled in the art, such as those described in *Advanced Organic Chemistry*, "Reactions, Mechanisms and Structures", J. March, 4th Ed., John Willey & Sons, NY, 1992.

The protected thiol dyes can be deprotected by conventional pathways such as those described in the books "*Protective Groups in Organic Synthesis*" T. W. Greene, John Willey & Sons Publisher, NY, 1981; "*Protecting Groups*", P. Kocienski, Thieme, 3rd Ed., 2005.

Another subject of the disclosure relates to a dye composition for dyeing keratin materials, which comprises at least one thiol/disulfide fluorescent dye of formula (I). In addition to the presence of at least one fluorescent dye of formula (I), the composition disclosed herein may also comprise a reducing agent.

This reducing agent may be chosen from thiols, for example cysteine, homocysteine or thiolactic acid, the salts of these thiols, phosphines, bisulfite, sulfites, thioglycolic acid, and also its esters, in particular glyceryl monothioglycolate, and thioglycerol. This reducing agent may also be chosen from borohydrides and derivatives thereof, for instance the salts of borohydride, of cyanoborohydride, of triacetoxyborohydride or of trimethoxyborohydride: sodium salts, lithium salts, potassium salts, calcium salts, quaternary ammonium (tetramethylammonium, tetraethylammonium, tetra-n-butylammonium or benzyltriethylammonium) salts; and catechol borane.

The dye composition that can be used in the disclosure generally comprises an amount of fluorescent dye of formula (I) ranging from 0.001% to 50%, relative to the total weight of the composition. For example, this amount may range from 0.005% to 20% by weight, such as from 0.01% to 5% by weight, relative to the total weight of the composition.

The dye composition may also comprise additional direct dyes. These direct dyes are, for example, chosen from neutral, acidic or cationic nitrobenzene direct dyes, neutral, acidic, or cationic azo direct dyes, tetraazapentamethine dyes, neutral, acidic, or cationic quinone, such as anthraquinone dyes, azine direct dyes, triarylmethane direct dyes, indoamine direct dyes, and natural direct dyes.

Among the natural direct dyes, mention may be made of lawsone, juglone, alizarin, purpurin, carminic acid, kermesic acid, purpurogallin, protocatechaldehyde, indigo, isatin, curcumin, spinulosin, and apigenindin. Extracts or decoctions comprising these natural dyes, such as poultices or henna-based extracts, may also be used.

The dye composition may comprise at least one oxidation base and/or at least one coupler conventionally used for dyeing keratin fibers.

Among the oxidation bases, mention may be made of para-phenylenediamines, bisphenylalkylenediamines, para-aminophenols, bis-para-aminophenols, ortho-aminophenols, heterocyclic bases, and addition salts thereof.

Among these couplers, mention may in particular be made of meta-phenylenediamines, meta-aminophenols, meta-diphenols, naphthalene couplers, heterocyclic couplers, and addition salts thereof.

The coupler(s) is (are) each generally present in an amount ranging from 0.001% to 10% by weight relative to the total weight of the dye composition, such as from 0.005% to 6%.

The oxidation base(s) present in the dye composition is (are) in general each present in an amount ranging from 0.001% to 10% by weight relative to the total weight of the dye composition, such as from 0.005% to 6% by weight.

In general, the addition salts of the oxidation bases and of the couplers that can be used in the context of the disclosure are for example chosen from addition salts with an acid, such as hydrochlorides, hydrobromides, sulfates, citrates, succinates, tartrates, lactates, tosylates, benzenesulfonates, phosphates and acetates, and addition salts with a base, such as hydroxides of an alkali metal such as sodium or potassium, aqueous ammonia, amines, or alkanolamines.

The medium suitable for dyeing, also called dye support, is a cosmetic medium generally constituted of water or of a mixture of water and at least one organic solvent. By way of organic solvent, mention may, for example, be made of $C_1$-$C_4$ lower alkanols, such as ethanol and isopropanol; polyols and polyol ethers, such as 2-butoxyethanol, propylene glycol, propylene glycol monomethyl ether, diethylene glycol monoethyl ether and diethylene glycol monomethyl ether, and also aromatic alcohols such as benzyl alcohol or phenoxyethanol, and mixtures thereof.

The solvents other than water, when they are present, are for example present in proportions for example ranging from 1% to 40% by weight approximately, relative to the total weight of the dye composition, such as from 5% to 30% by weight approximately. The solvents, including water, are for example present in proportions for example ranging from 1% to 99% by weight approximately, relative to the total weight of the dye composition, such as from 5% to 95% by weight approximately.

According to one embodiment, the composition of the disclosure comprises a reducing agent capable of reducing the disulfide bonds of keratin and/or the disulfide bonds of the fluorescent dyes of formula (I). This reducing agent is as defined above.

The dye composition may also comprise various adjuvants conventionally used in hair-dyeing compositions, such as anionic, cationic, nonionic, amphoteric, or zwitterionic surfactants or mixtures thereof, anionic, cationic, nonionic, amphoteric, or zwitterionic polymers, or blends thereof, mineral or organic thickeners, and in particular anionic, cationic, nonionic and amphoteric associative polymer thickeners, antioxidants, penetrating agents, sequestering agents, fragrances, buffers, dispersing agents, conditioning agents such as, for example, modified or unmodified, volatile or nonvolatile silicones, such as amino silicones, film-forming agents, ceramides, preservatives, opacifiers or conductive polymers.

The above adjuvants are in general present in an amount, for each of them, ranging from 0.01% to 20% by weight relative to the total weight of the composition.

Of course, those skilled in the art will take care to select this or these possible additional compounds in such a way that the advantageous properties intrinsically associated with the dye composition disclosed herein are not, or are not substantially, impaired by the addition(s) envisaged.

The pH of the dye composition generally ranges from 3 to 14 approximately, for example from 5 to 11 approximately. It may be adjusted to the desired value by means of acidifying or basifying agents normally used in the dyeing of keratin fibers or else by means of conventional buffer systems.

Among the acidifying agents, mention may, by way of example, be made of mineral or organic acids, such as hydrochloric acid, orthophosphoric acid, sulfuric acid, carboxylic acids, for instance acetic acid, tartaric acid, citric acid or lactic acid, or sulfonic acids.

Among the basifying agents, mention may, by way of example, be made of aqueous ammonia, alkali carbonates, alkanolamines such as mono-, di- and triethanolamines, and also derivatives thereof, sodium hydroxide or potassium hydroxide and the compounds of formula (γ) below:

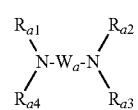

(γ)

wherein $W_a$ represents a propylene residue optionally substituted with a hydroxyl group or a $C_1$-$C_4$ alkyl radical; $R_{a1}$, $R_{a2}$, $R_{a3}$ and $R_{a4}$, which may be identical or different, are chosen from a hydrogen atom, a $C_1$-$C_4$ alkyl radical or a $C_1$-$C_4$ hydroxyalkyl radical.

The dye composition may be in various forms, such as in the form of a liquid, a cream or a gel, or in any other form suitable for dyeing keratin fibers, such as hair.

Also disclosed herein is a process for dyeing keratin material comprising applying a composition comprising at least one dye of formula (I) to said materials. According to one embodiment disclosed herein, a reducing agent may also be applied as a pretreatment before the application of the composition comprising at least one fluorescent dye of formula (I).

This reducing agent may be chosen from thiols, for example cysteine, homocysteine or thiolactic acid, the salts of these thiols, phosphines, bisulfite, sulfites, thioglycolic acid, and also its esters, such as glyceryl monothioglycolate, and thioglycerol. This reducing agent may also be chosen from borohydrides and derivatives thereof, for instance the salts of borohydride, of cyanoborohydride, of triacetoxyborohydride or of trimethoxyborohydride: sodium salts, lithium salts, potassium salts, calcium salts, quaternary ammonium (tetramethylammonium, tetraethylammonium, tetra-n-butylammonium or benzyltriethylammonium) salts; and catechol borane.

This pretreatment may be of short duration, for example ranging from 1 second to 30 minutes, such as from 1 minute to 15 minutes, with a reducing agent as mentioned above.

According to another embodiment, the composition comprising at least one fluorescent dye of formula (I) also comprises at least one reducing agent as defined above. This composition is then applied to the hair.

When the thiol fluorescent dye of formula (I) where n=m=1 comprises a thiol-function-protecting group Y, the process of the disclosure may be preceded by a deprotection step aimed at restoring the SH function in situ.

By way of example, it is possible to deprotect the S—Y function with a Y protecting group by adjusting the pH as follows:

| Y: Protecting group | Deprotection |
|---|---|
| alkylcarbonyl | pH > 9 |
| arylcarbonyl | pH > 9 |
| alkoxycarbonyl | pH > 9 |
| aryloxycarbonyl | pH > 9 |
| arylalkoxycarbonyl | pH > 9 |
| (di)(alkyl)aminocarbonyl | pH > 9 |
| (alkyl)arylaminocarbonyl | pH > 9 |
| optionally substituted aryl, such as phenyl | pH > 9 |
| 5-, 6- or 7-membered monocyclic heteroaryl such as oxazolium | pH > 9 |
| 8- to 11-membered bicyclic heteroaryl, such as benzoimidazolium or benzoxazolium | pH > 9 |

The deprotection step can also be carried out during a hair pretreatment step, for instance reducing pretreatment of the hair.

According to one embodiment, the reducing agent is added to the dye composition comprising at least one fluorescent dye of formula (I) at the time of use.

According to another embodiment, the composition comprising at least one fluorescent dye of formula (I) also comprises at least one reducing agent as defined above. This composition is then applied to the hair.

According to another embodiment, the reducing agent is applied as a post-treatment, after the application of the composition comprising at least one fluorescent dye of formula (I). The duration of the post-treatment with the reducing agent may be short, for example ranging from 1 second to 30 minutes, such as from 1 minute to 15 minutes, with a reducing agent as described above. According to one embodiment, the reducing agent comprises an agent of thiol or borohydride type as described above.

Another embodiment disclosed herein is a process wherein the fluorescent dye of formula (I) can be applied directly to the hair without reducing agents, free of reducing pretreatment or reducing post-treatment.

A treatment with an oxidizing agent may optionally be combined. Any type of oxidizing agent conventional in the field may be used. Thus, it may be chosen from hydrogen peroxide, urea peroxide, alkali metal bromates, persalts such as perborates and persulfates, and also enzymes, among which mention may be made of peroxidases, 2-electron oxidoreductases such as uricases and 4-electron oxygenases such as laccases. The use of hydrogen peroxide is one example.

This oxidizing agent can be applied to the fibers before or after the application of the composition comprising at least one fluorescent dye of formula (I).

The application of the dye composition disclosed herein is generally carried out at ambient temperature. It may, however, be carried out at temperatures ranging from 20 to 180° C.

A subject of the disclosure is also a multicompartment dyeing device or dyeing "kit" in which a first compartment comprises a dye composition comprising at least one fluorescent dye of formula (I) and a second compartment comprises a reducing agent capable of reducing the disulfide functions of keratin materials and/or of the disulfide fluorescent dye of formula (I), when n is 2 and m is 0.

One of these compartments may also comprise one or more other dyes of direct dye or oxidation dye type.

Also disclosed herein is a multicompartment device in which a first compartment comprises a dye composition comprising at least one fluorescent dye of formula (I); a second compartment comprises a reducing agent capable of reducing the disulfide bond of keratin materials and/or of the disulfide fluorescent dye of formula (I), when n is 2 and m is 0; and a third compartment comprises an oxidizing agent.

Alternatively, the dyeing device comprises a first compartment comprising a dye composition which comprises at least one protected thiol fluorescent dye of formula (I) when n=m=1, and a second compartment comprising an agent capable of deprotecting the protected thiol so as to free the thiol.

Each of the devices mentioned above may be equipped with a means for delivering the desired mixture to the hair, for example such as the devices described in French Patent No. FR 2 586 913.

The examples which follow serve to illustrate the disclosure without, however, being limiting in nature. The thiol fluorescent dyes of the examples hereinafter have been entirely characterized by conventional spectroscopic and spectrometric methods.

Other than in the examples, or where otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present disclosure. At the very least, and not as an attempt to limit the application of the doctrine of equivalents to the scope of the claims, each numerical parameter should be construed in light of the number of significant digits and ordinary rounding approaches.

Notwithstanding that the numerical ranges and parameters setting forth the broad scope of the disclosure are approximations, unless otherwise indicated the numerical values set forth in the specific examples are reported as precisely as possible. Any numerical value, however, inherently contains certain errors necessarily resulting from the standard deviation found in their respective testing measurements.

The examples that follow are intended to illustrate the present disclosure without, however, being limiting in nature.

EXAMPLES
Synthesis Examples
Example 1
Synthesis of 1,1'-{disulfanediylbis[ethane-2,1-diylimino(2-oxoethane-2,1-diyl)]}bis[4-(−2-{4-[bis(2-hydroxyethyl)amino]phenyl}vinyl)pyridinium] dichloride [1]
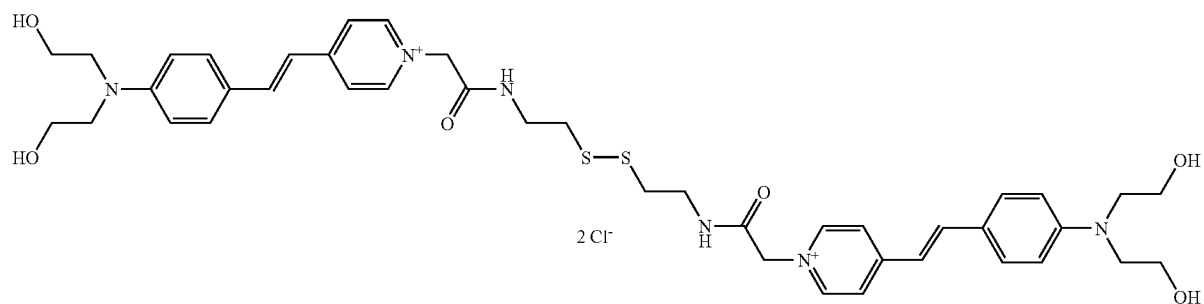
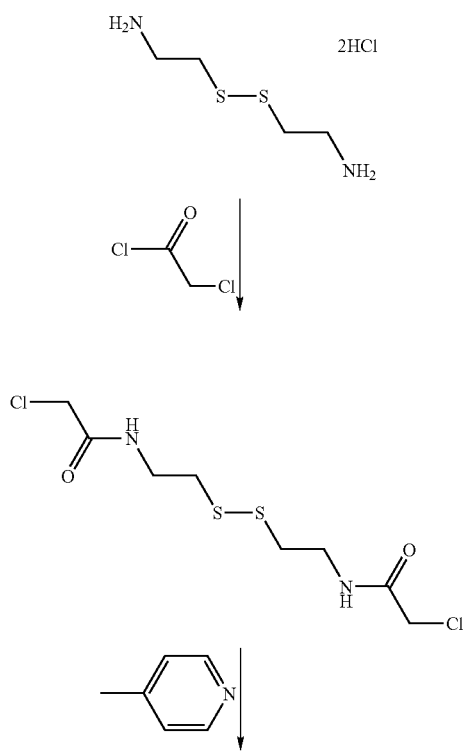
Synthesis scheme

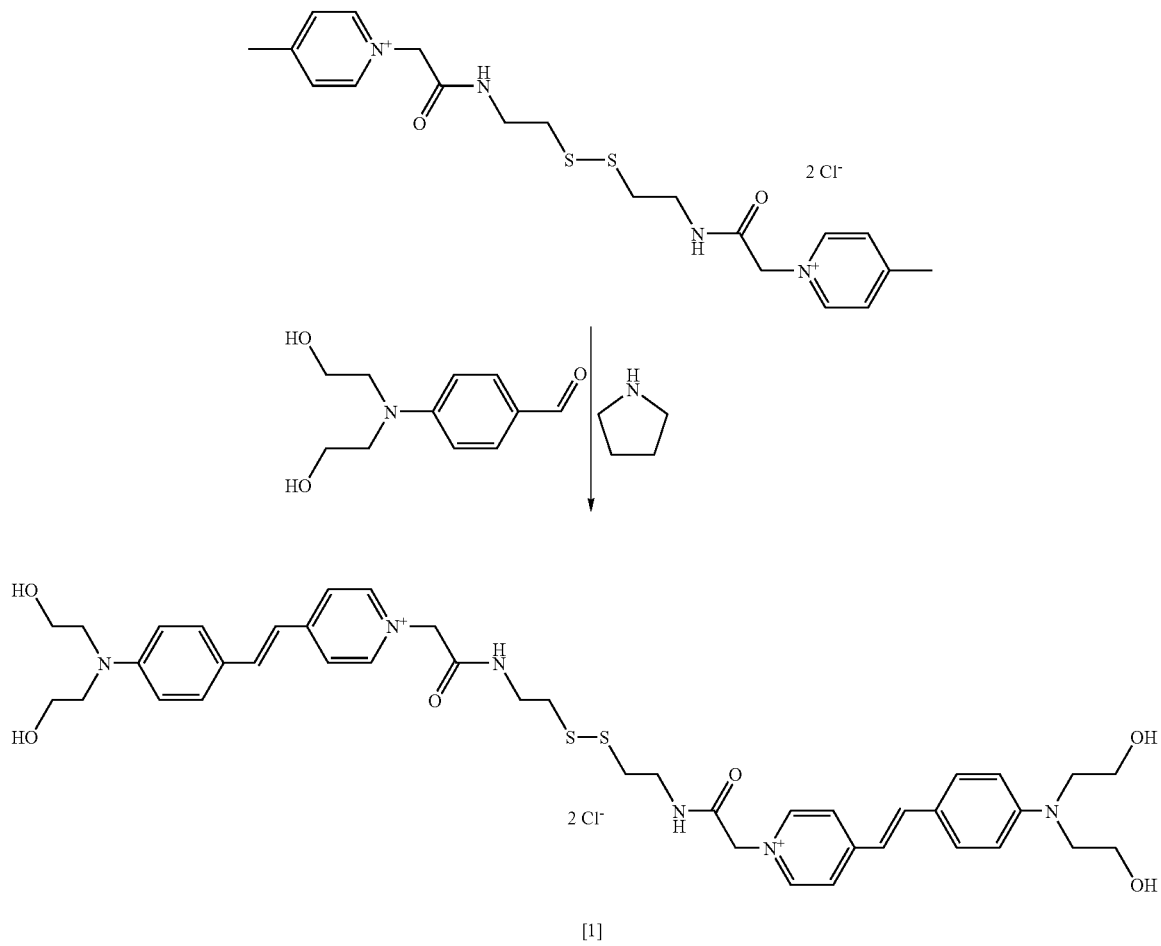

Stage 1: Synthesis of N,N'-(disulfanediyldiethane-2,1-diyl)bis(2-chloroacetamide)

40.3 g of cystamine dihydrochloride qA dissolved in 100 ml of water, 32 ml of sodium hydroxide at 35% was added (pH 9.7) and the temperature was reduced to 5°. 33.5 ml of chloroacetyl chloride was introduced dropwise, while a temperature below 10° C. was maintained and the pH between 7.9 and 9.3 was maintained by adding sodium hydroxide. The medium was stirred at ambient temperature for 2 h. The precipitate was filtered off, washed with 5×150 ml of water, and then dried under vacuum in the presence of $P_2O_5$. 35.3 g of white powder was recovered. The analyses indicated that the product was in conformity.

Stage 2: Synthesis of 1,1'-{disulfanediylbis[ethane-2,1-diylimino(2-oxoethane-2,1-diyl)]}bis(4-methylpyridinium)dichloride 6.1 g of N,N'-(disulfanediyldiethane-2,1-diyl)bis(2-chloroacetamide) and 4.5 g of 4-picoline was dissolved in 50 ml of NMP and brought to 80° C. for 19 h. After cooling the mixture, with successive precipitations from acetone and drying under vacuum, 9.2 g of salts were recovered. The analyses showed that the product was in conformity. $^1$H NMR (400 MHz, $D_2O$): 2.61 (s, 6H), 2.82 (t, 4H), 3.56 (t, 4H), 5.31 (s, 4H), 7.85 (d, 4H), 8.51 (d, 4H).

Stage 3: Synthesis of 1,1'-{disulfanediylbis[ethane-2,1-diylimino(2-oxoethane-2,1-diyl)]}bis[4-(2-{4-[bis(2-hydroxyethyl)amino]phenyl}vinyl)pyridinium] dichloride [1]

837 mg of 4-[bis(2-hydroxyethyl)amino]benzaldehyde, 328 μl of pyrrolidine, 232 μl of acetic acid and 490 mg of 1,1'-{disulfanediylbis[ethane-2,1-diylimino(2-oxoethane-2,1-diyl)]}bis(4-methylpyridinium) dichloride were solubilized in 10 ml of isopropanol and stirred at ambient temperature for 3 h 30 min. The mixture was poured into 50 ml of a 1:1 solution of dichloromethane/acetone. An oil separated by settling out, and it was dried under vacuum. 442 mg of black powder were recovered. The analyses showed that the product was in conformity.

Example 2

1,1'-{disulfanediylbis[ethane-2,1-diylimino(2-oxoethane-2,1-diyl)]}bis(4-{2-[4-(3-hydroxypyrrolidin-1-yl)phenyl]vinyl}pyridinium)dichloride

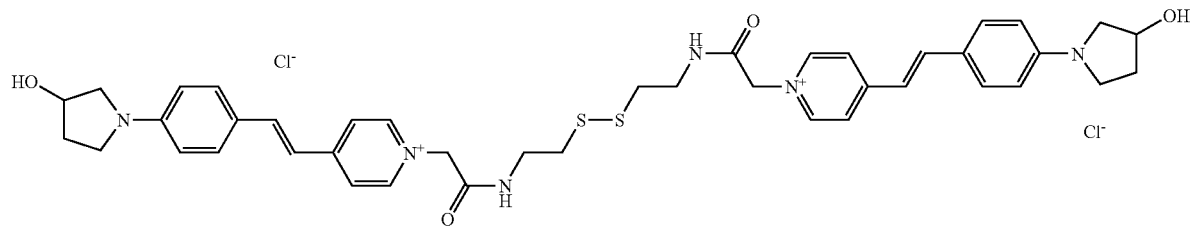

[2]

Synthesis scheme

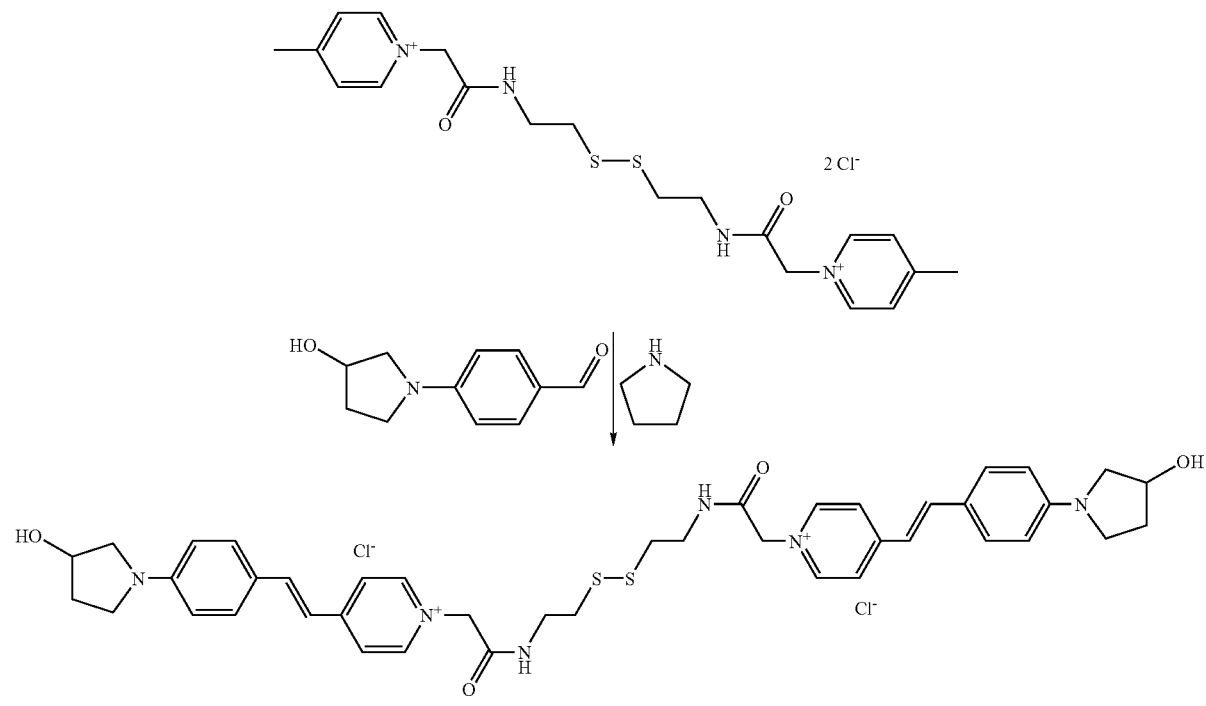

19.88 g of 4-(3-hydroxypyrrolidin-1-yl)benzaldehyde, 7.17 g of pyrrolidine, 6.05 g of acetic acid and 24.8 g of 1,1'-{disulfanediylbis[ethane-2,1-diylimino(2-oxoethane-2,1-diyl)]}bis(4-methylpyridinium)dichloride were solubilized in 200 ml of ethanol and stirred at ambient temperature for 48 h. The mixture was filtered, and washed with 3 times 100 ml of isopropanol. 43.19 g of black powder were recovered and then recrystallized from a mixture of 200 ml of ethanol, 50 ml of methanol, and 25 ml of water. After filtration and drying under vacuum, 35.8 g of brick-red powder were obtained. The analyses showed that the product was in conformity.

Example 3

Synthesis of 2,2'-{disulfanediylbis[ethane-2,1-diylimino(4-oxobutane-4,1-diyl)pyridinium-1,4-diylethene-2,1-diylbenzene-4,1-diyl(methylimino)]}-diacetate

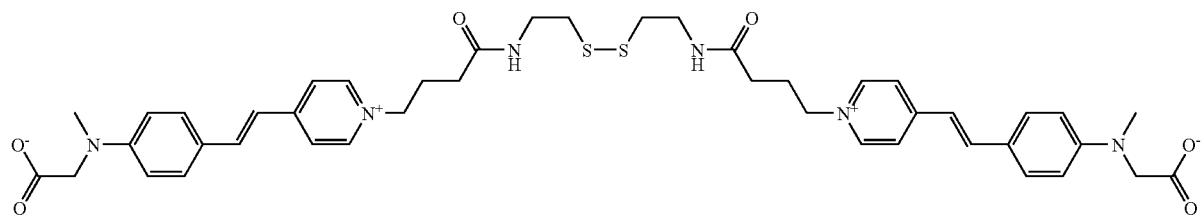

[3]

Synthesis scheme

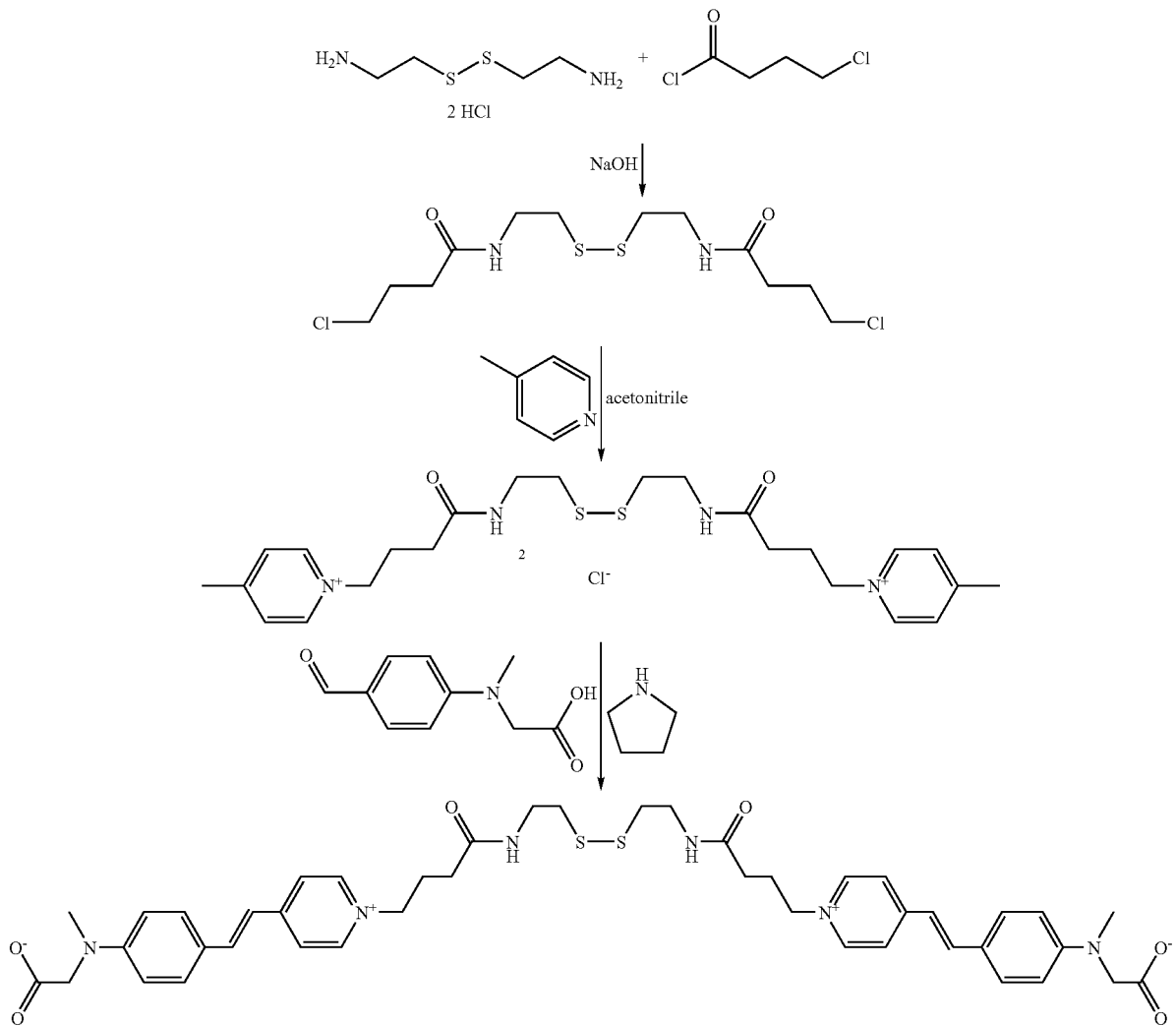

Step 1: Synthesis of N,N'-(disulfanediyldiethane-2,1-diyl)bis(4-chlorobutanamide)

60 g of cystamine hydrochloride was solubilized in 500 mL and cooled to 5° C. The pH was raised to 10 by addition of aq. NaOH (30%). A solution of 4-chlorobutanoyl chloride (105 g) in anhydrous THF (500 mL), was added dropwise, while the pH was maintained above 7 by addition of aq. NaOH (30%). After completion of the addition and stabilization of pH at 7, the mixture mixed for 3 days. The aqueous layer was extracted with 3×500 mL dichloromethane, combined with THF layer and dried over Na$_2$SO$_4$. After drying under vacuum, 41 g of a white powder were collected. Analyses were in accordance with the expected structure.

Step 2: Synthesis 1,1'-{disulfanediylbis[ethane-2,1-diylimino(4-oxobutane-4,1-diyl)]}bis(4-methyl-pyridinium)dichloride 30 g of N,N'-(disulfanediyldiethane-2,1-diyl)bis(4-chlorobutanamide) were dispersed in 100 mL acetonitrile, 20.2 mL of 4-pioline were added and the reaction mixture was stirred at 80° C. for 2 days. After cooling at room temperature, the solvent was removed by evaporation and the resulting oil was washed several times with ethyl acetate. 44.2 g of a light brown solid was collected. Analyses were in accordance with the expected structure.

Step 3: Synthesis of 2,2'-{disulfanediylbis[ethane-2,1-diylimino(4-oxobutane-4,1-diyl)pyridinium-1,4-diylethene-2,1-diylbenzene-4,1-diyl(methylimino)]}-diacetate 16.7 g of [(4-formylphenyl)(methyl)amino]acetic acid and 6.3 g of pyrrolidine were mixed in 50 mL isopropanol at 80° C. After 15 minutes, 1.46 g of pyrrolidine was added followed by a solution of 22.5 g de 1,1'-{disulfanediylbis[ethane-2,1-diylimino(4-oxobutane-4,1-diyl)]}bis(4-methylpyridinium) dichloride in 100 mL isopropanol. The reaction mixture was heated for 2 hours, the mixture was cooled at room temperature, then poured on 1.4 L acetone. A precipitate formed, it was filtered under argon, washed three times with 170 mL of acetone and dried. The resulting solid was dispersed in 400 mL isopropanol and 400 mL water and 1.2 L of acetone were added. The resulting oil was dissolved in 50 mL methanol and 750 mL acetone were added. The sticky dark brown oil was triturate in 500 mL acetone, filtered and dried. 20.5 g of black powder was collected.

Analyses were in agreement with the expected structure.

NMR $^1$H CD$_3$OD ppm: 2.33 (m, 4H), 2.48 (t, 4H), 2.98 (t, 4H), 3.31 (s, 6H), 3.59 (t, 4H), 4.54 (t, 4H), 6.83 (d, 4H), 6.99 (d, 2H), 7.59 (d, 4H) 7.75 (d, 2H), 7.86 (d, 4H), 8.56 (d, 4H).

Example 4

Synthesis of 1,1'-{disulfanediylbis[ethane-2,1-diylimino(4-oxobutane-4,1-diyl)]}bis{4-[2-{4-[bis-(2-hydroxyethyl)amino]phenyl}ethenyl]pyridinium}dichloride

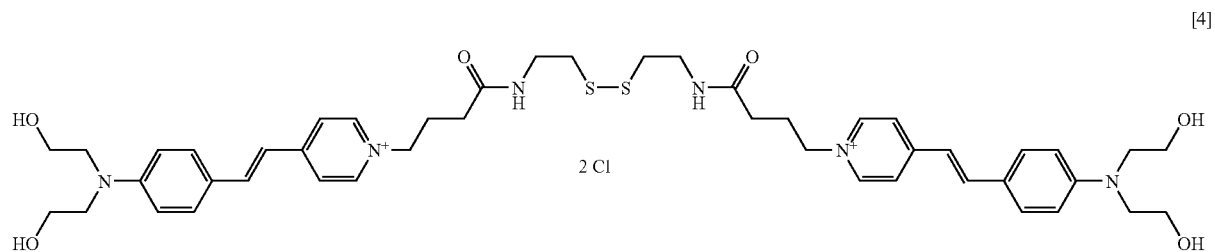

[4]

Synthesis scheme

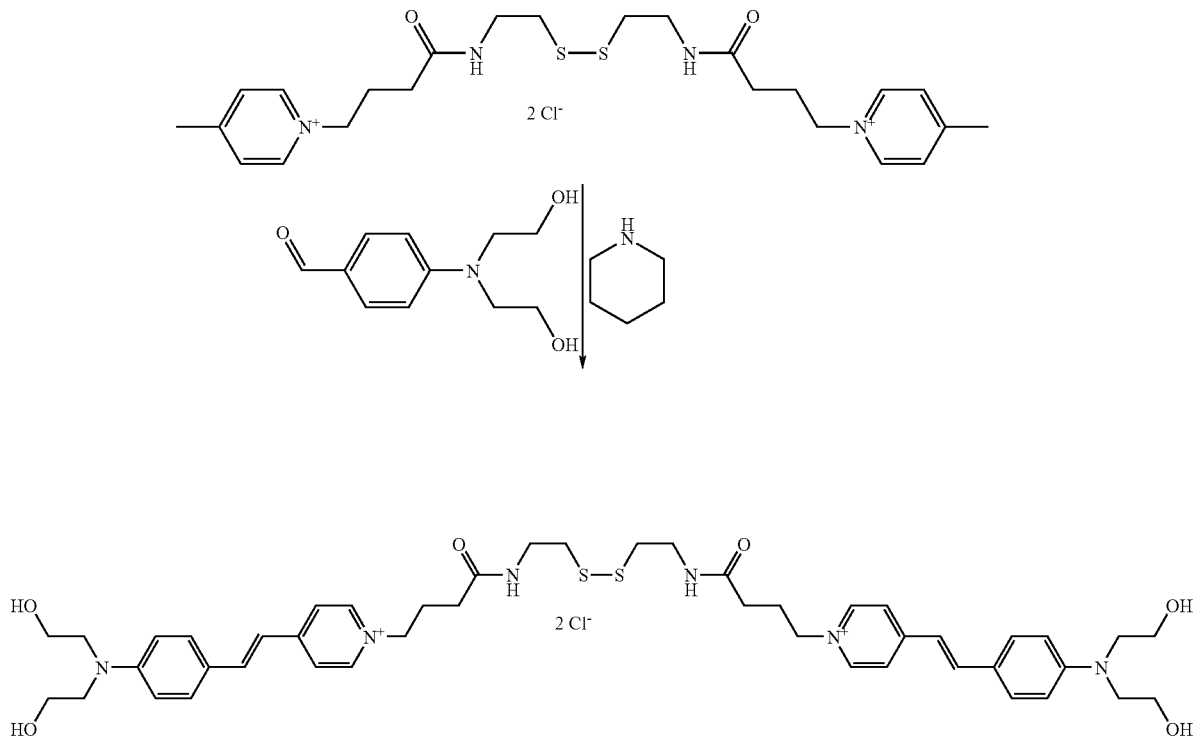

20 g of 1,1'-{disulfanediylbis[ethane-2,1-diylimino(4-oxobutane-4,1-diyl)]}bis(4-methylpyridinium)dichloride, 1.8 mL of piperidine and 16 g of 4-[bis-(2-hydroxy-ethyl)-amino]-benzaldehyde were mixed together in 60 mL isopropanol at 70° C. for 18 hours. After cooling at room temperature, the supernatant solution was discarded, the resulting oil was washed three times with hot isopropanol (100 mL, 2 h at 80° C.). The oil was diluted in 500 mL of water, frozen and lyophilized. 24 g of a fluffy dark red powder was obtained.

Analyses were in accordance with the expected structure

NMR $^1$H CD$_3$OD ppm 2.25 (m, 4H), 2.36 (t, 4H), 2.81 (t, 4H), 3.45 (t, 4H), 3.64 (t, 8H), 3.76 (t, 8H), 4.46 (t, 4H), 6.83 (d, 4H), 7.07 (d, 2H), 7.59 (d, 4H), 7.82 (d, 2H), 7.96 (d, 4H), 8.57 (d, 4H), LC/MS gradient ACONH$_4$ 20 mM->CH3CN 10 min ESI+ m/z=429

Example 5

Synthesis of 2,2'-{disulfanediylbis[ethane-2,1-diylimino(4-oxobutane-4,1-diyl)pyridinium-1,2-diylethene-2,1-diylbenzene-4,1-diyl(methylimino)]}-diacetate

[5]

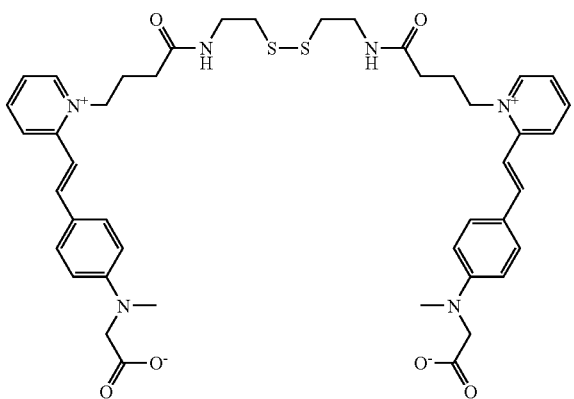

Synthesis scheme

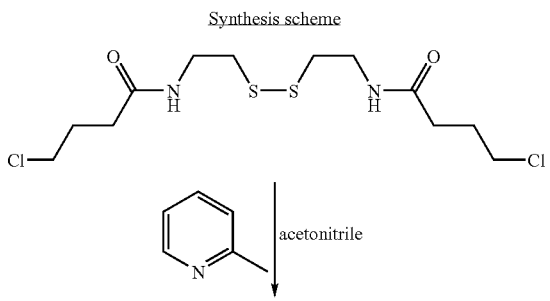

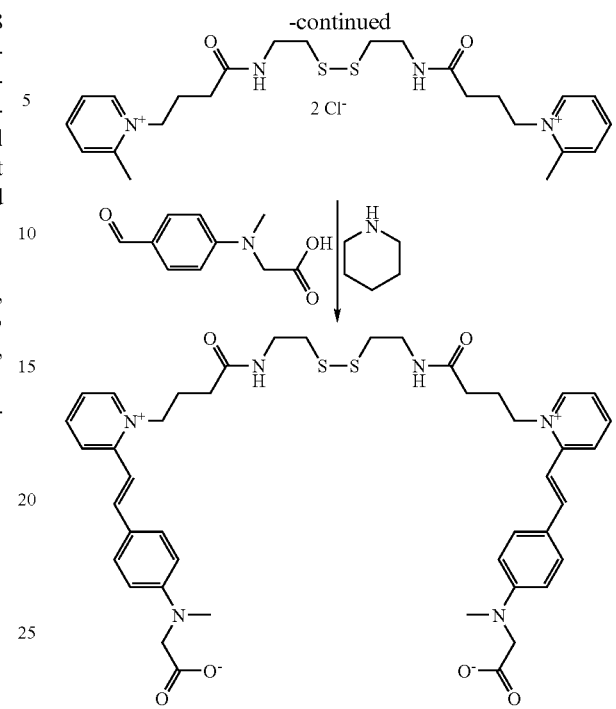

Step 1: Synthesis 1,1'-{disulfanediylbis[ethane-2,1-diylimino(4-oxobutane-4,1-diyl)]}bis(2-methyl-pyridinium)dichloride 1.13 g of N,N'-(disulfanediyldiethane-2,1-diyl)bis(4-chlorobutanamide) was dispersed in 0.5 mL of N-methylpyrrolidinone and 2.5 mL acetonitrile and heated at 50° C. 0.71 mL of picoline was added and the reaction mixture was stirred for 5 days at 50° C. A few milligrams of cesium carbonate and additional 0.35 mL of 2-picoline were added. After one day at 65° C., the reaction mixture was poured in 50 mL acetonitrile. The resulting gum was washed several times with ethyl acetate, solubilized in ethanol, filtered and dried under vacuum. 0.95 g of a beige solid were obtained.

Analyses were in accordance with the expected structure and the compound was used as such for following steps.

LC/MS gradient ACONH$_4$ 20 mM->CH$_3$CN 10 min ESI+ m/z=238 (dication)

Step 2: Synthesis of 2,2'-{disulfanediylbis[ethane-2,1-diylimino(4-oxobutane-4,1-diyl)pyridinium-1,2-diylethene-2,1-diylbenzene-4,1-diyl(methylimino)]}-diacetate 0.35 g of [(4-formylphenyl)(methyl)amino]acetic acid, 0.47 g of 1,1'-{disulfanediylbis[ethane-2,1-diylimino(4-oxobutane-4,1-diyl)]}bis(4-methylpyridinium) dichloride and 42 μL of piperidine were mixed in 3 mL methanol at 70° C. for 2 h. The reaction mixture was poured in 25 mL ethyl acetate and the precipitate was filtered and dried. A black powder was obtained. Analyses showed that the expected product was obtained. LC/MS gradient ACONH$_4$ 20 mM->CH$_3$CN 10 min ESI+ m/z=413

Example 6

Synthesis of 1,1'-{disulfanediylbis[ethane-2,1-diylimino(4-oxobutane-4,1-diyl)]}bis{2-[-2-{4-[bis(2-hydroxyethyl)amino]phenyl}ethenyl]pyridinium}dichloride

[6]

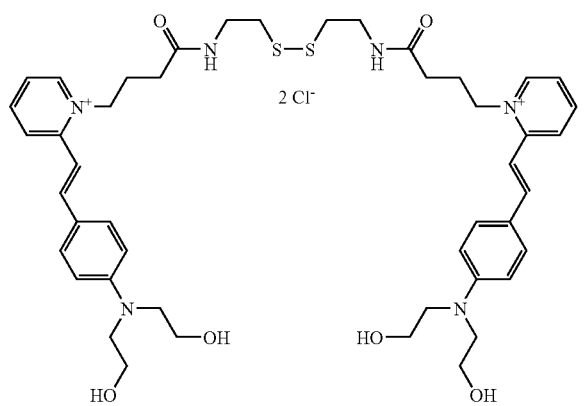

Synthesis scheme

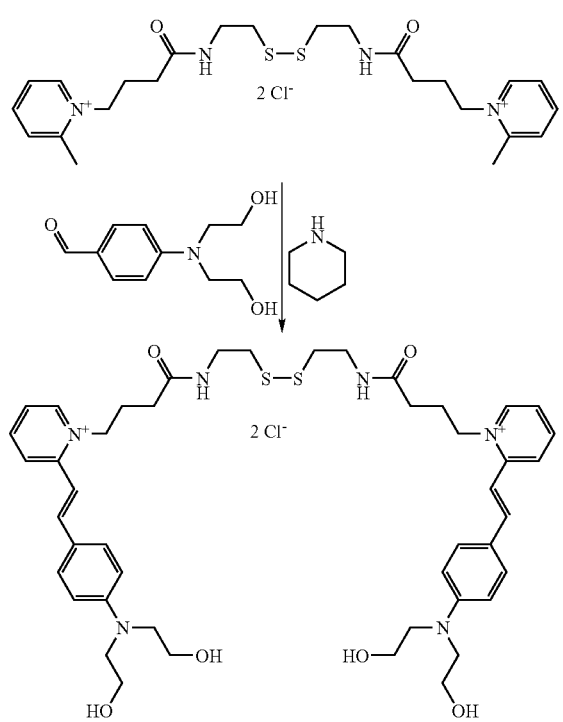

0.37 g of 4-[bis-(2-hydroxy-ethyl)-amino]-benzaldehyde, 0.47 g of 1,1'-{disulfanediylbis[ethane-2,1-diylimino(4-oxobutane-4,1-diyl)]}bis(4-methylpyridinium) dichloride and 42 μL of piperidine were mixed in 3 mL methanol at 70° C. for 2 h. The reaction mixture was poured in 25 mL ethyl acetate and the precipitate was filtered and dried. A black powder was obtained. Analyses showed that the expected product was obtained. LC/MS gradient ACONH$_4$ 20 mM->CH3CN 10 min ESI+ m/z=429

Dyeing Example

Example 1

Dyeing Process—Compound [1]

Preparation of a Composition A

| | |
|---|---|
| Compound [1] | $5 \times 10^{-4}$ mol % |
| Benzyl alcohol | 4 g |
| Polyethylene glycol 6 EO | 6 g |
| Hydroxyethylcellulose | 0.7 g |
| Alkylpolyglucoside in an aqueous solution containing 65% AM | 4.5 g |
| Demineralized water | qs 100 g |

Preparation of a Composition B

| | |
|---|---|
| Thioglycolic acid | 1M |
| Sodium hydroxide | qs pH 8.5 |
| Demineralized water | qs 100 g |

At the time of use, compositions A (9 ml) and B (1 ml) were mixed, then the formulations were applied to locks of natural white hair containing 90% white hairs (NW), permanent-waved white hair (PW), or dark hair having a tone height of 4 (TH4). The leave-in time was 20 minutes at ambient temperature (AT).

After rinsing with running water, a fixer (Dulcia Vital II®) diluted 10-fold with water was applied for 5 minutes at AT. After rinsing with running water and shampooing, the locks were air-dried and lightening of the dark hair thus treated was observed: the TH4 lock became visually lighter than the untreated control locks. The locks of white hair were colored with strong shades.

Visual Observations:

During the rinsing and shampooing operations of example [1], there was no visible bleeding of the color; the shampoo foam and the rinsing water were virtually uncolored.

The color observed was conserved on the dyed NW and PW, and the lightening effect remained visible on the shampooed TH4 hair.

Test for Fastness with Respect to Shampooing Operations

The treated locks were washed with a series of 24 shampooing operations. It was observed that the foam of the shampoos was uncolored or virtually uncolored and that the color did not become dull over time on the NW and PW locks. The lightening effect also remained intact.

Reflectance Results for Evaluating the Optical Lightening:

The lightening effectiveness of the compositions in accordance with the disclosure was expressed as a function of the reflectance of the hair. These reflectances were compared with the reflectance of a lock of untreated hair of tone height TH4.

The reflectance was measured by means of a KONIKA-MINOLTA®, CM 3600d spectrophotocolorimeter apparatus and after irradiation of the hair with visible light in the wavelength range of from 400 to 700 nanometers.

FIG. 1 shows the reflectance values of a reference lock (a lock of untreated hair of tone height TH4) and the reflectance values of TH4 locks treated with compound 1 at application and after 24 shampooing operations.

It was noted that the reflectance of a lock of hair treated with a composition according to the disclosure was greater than that of untreated hair. For example, the reflectance of the locks treated with dye [1] was much greater than that of the reference lock in the wavelength range above 580 nm. The locks treated with this compound therefore appeared to be lighter. It was also noted that the effect was completely retained after 24 shampooing operations.

Results in the L*a*b* System for Evaluating the Coloring of the Locks NR, PW:

The color of the locks was evaluated in the L*a*b* system by means of a MINOLTA® CM 3600D spectrocolorimeter (Illuminant D65).

In this L*a*b* system, L* represents the lightness, a* indicates the green/red color axis and b* the blue/yellow color axis. The higher the value of L, the lighter or weaker the color. Conversely, the lower the value of L, the darker or much stronger the color. The higher the value of a*, the redder the shade, and the higher the value of b*, the more yellow the shade.

The variation in coloring between the TH4 dyed and washed locks of hair was measured by ($\Delta E$) according to the following equation:

$$\Delta E = \sqrt{(L^* - L_o^*)^2 + (a^* - a_o^*)^2 + (b^* - b_o^*)^2}$$

In this equation, L*, a* and b* represent the values measured before dyeing, and $L_o^*$, $a_o^*$ and $b_o^*$ represent the values measured before dyeing (or shampooing).

The greater the value of $\Delta E$, the greater the difference in color between the TH4 locks and the colored locks.

|  | L* | a* | b* | dE* |
|---|---|---|---|---|
| NW reference | 59.9 | 1.1 | 11.5 | — |
| Compound 1 | 36.3 | 38.1 | 23.8 | 45.6 |
| After 24 shampooing operations | 39.0 | 37.7 | 21.9 | 43.4 |
| PW reference | 58.6 | 0.7 | 12.2 | — |
| Compound 1 | 32.4 | 40.8 | 26.1 | 49.9 |
| After 24 shampooing operations | 31.8 | 40.2 | 23.6 | 49.1 |

The natural white hair and the permanent-waved white hair were colored bright orangey-red. The values changed very little after the shampooing operations, given the number of successive shampooing operations.

What is claimed is:

1. A fluorescent dye of formula (I):

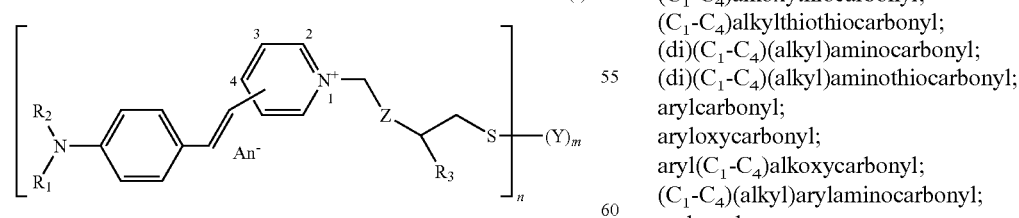

the organic or mineral acid salts thereof, optical isomers and geometric isomers thereof, or the solvates thereof;
wherein in formula (I):
$R_1$ is chosen from a $C_1$-$C_6$ alkyl group substituted with at least one hydroxyl group or —C(O)OR' group, wherein R' is chosen from a hydrogen atom, a $C_1$-$C_4$ alkyl group, or a —C(O)—O⁻ group, wherein when R' is a —C(O)—O⁻ group an anionic counterion An⁻ is absent;
$R_2$ is chosen from a $C_1$-$C_6$ alkyl group optionally substituted with at least one hydroxyl group;
or else the groups $R_1$ and $R_2$ form, together with the nitrogen which bears them, a saturated heterocyclic radical substituted at least with a hydroxyl, (poly)hydroxy($C_1$-$C_4$)alkyl, and/or —C(O)OR' group, with R' chosen from a hydrogen atom, a $C_1$-$C_4$ alkyl group or a —C(O)—O⁻ group, wherein when R' is a —C(O)—O⁻ group an anionic counterion An⁻ is absent;
$R_3$ is chosen from a hydrogen atom or a —C(O)OR'' group, with R'' chosen from a hydrogen atom, an alkali metal or a $C_1$-$C_6$ alkyl group, or else $R_3$ is chosen from a —C(O)—O⁻ group and, in this case, an anionic counterion An⁻ is absent;
Z is chosen from a divalent amido —C(O)—N(R)— or —N(R)—C(O)— group, or a divalent $C_1$-$C_{10}$ alkylene group interrupted with an amido —C(O)—N(R)— or —N(R)—C(O)— group wherein R is chosen from a hydrogen atom or a $C_1$-$C_6$ alkyl group;
n is an integer ranging from 1 to 2;
m is an integer ranging from 0 to 1;
An⁻ represents an anionic counterion;
Y is chosen from: i) a hydrogen atom, ii) an alkali metal, iii) an alkaline earth metal, iv) an ammonium group: N⁺R$^\alpha$R$^\beta$R$^\gamma$R$^\delta$, a phosphonium group: P⁺R$^\alpha$R$^\beta$R$^\gamma$R$^\delta$ with R$^\alpha$, R$^\beta$, R$^\gamma$ and R$^\delta$, which may be identical or different, are chosen from a hydrogen atom or a ($C_1$-$C_4$)alkyl group, or v) a thiol-function-protecting group;
wherein:
the bond between the pyridinium ring and the double bond of the styryl group is positioned in the 2- or 4-position with respect to the pyridinium;
when n=1, m=1, then Y=H or a thiol-function-protecting group and when n=2, then m=0;
when the compound of formula (I) comprises other cationic parts, it is associated with one or more anionic counterions which allow formula (I) to achieve electroneutrality.

2. The fluorescent dye according to claim 1, wherein Y is chosen from a hydrogen atom or an alkali metal.

3. The fluorescent dye according to claim 1, wherein Y is chosen from a protecting group.

4. The fluorescent dye according to claim 3, wherein Y is chosen from a protecting group chosen from the following radicals:
($C_1$-$C_4$)alkylcarbonyl;
($C_1$-$C_4$)alkylthiocarbonyl;
($C_1$-$C_4$)alkoxycarbonyl;
($C_1$-$C_4$)alkoxythiocarbonyl;
($C_1$-$C_4$)alkylthiothiocarbonyl;
(di)($C_1$-$C_4$)(alkyl)aminocarbonyl;
(di)($C_1$-$C_4$)(alkyl)aminothiocarbonyl;
arylcarbonyl;
aryloxycarbonyl;
aryl($C_1$-$C_4$)alkoxycarbonyl;
($C_1$-$C_4$)(alkyl)arylaminocarbonyl;
carboxyl;
$SO_3^-$; M⁺ with M⁺ representing an alkali metal or else An⁻ of formula (I) and M⁺ are absent;
optionally substituted aryl;
optionally substituted heteroaryl;
optionally cationic, optionally substituted heterocycloalkyl, the following group:

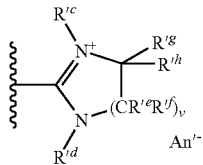

wherein R'^c, R'^d, R'^e, R'^f, R'^g and R'^h, which may be identical or different, are chosen from a hydrogen atom or a ($C_1$-$C_4$) alkyl group, or else two groups R'^g with R'^h, and/or R'^e with R'^f form an oxo or thioxo group, or else R'^g with R'^e together form a cycloalkyl; and v is chosen from an integer between 1 and 3 inclusive; such as R'^c to R'^h are a hydrogen atom; and An'$^-$ represents an anionic counterion;

isothiouronium;

—C(NR'^cR'^d)=N$^+$R'^eR'^f; An'$^-$ with R'^c, R'^d, R'^e and R'^f, which may be identical or different, are chosen from a hydrogen atom or a ($C_1$-$C_4$)alkyl group and An$^-$ being as defined above;

a isothiourea;

—C(NR'^cR'^d)=NR'^e; An'$^-$ with R'^c, R'^d, R'^e and An$^-$ as defined above;

optionally substituted (di)aryl($C_1$-$C_4$)alkyl;

optionally substituted (di)heteroaryl($C_1$-$C_4$)alkyl;

—CR$^1$R$^2$R$^3$ with R$^1$, R$^2$ and R$^3$, which may be identical or different, are chosen from a halogen atom or a group chosen from:

i) ($C_1$-$C_4$)alkyl;

ii) ($C_1$-$C_4$)alkoxy;

iii) optionally substituted aryl;

iv) optionally substituted heteroaryl;

v) P(Z$^1$)R'^1R'^2R'^3 with R'^1 and R'^2, which may be identical or different, are chosen from a hydroxyl, ($C_1$-$C_4$)alkoxy or alkyl group, R'^3 is chosen from a hydroxyl or ($C_1$-$C_4$) alkoxy group, and Z$^1$ is chosen from an oxygen or sulfur atom;

a sterically hindered cyclic group; and optionally substituted alkoxyalkyl.

5. The fluorescent dye according to claim 1, wherein Y is chosen from an alkali metal or a protecting group chosen from:

($C_1$-$C_4$)alkylcarbonyl;

arylcarbonyl;

($C_1$-$C_4$)alkoxycarbonyl;

aryloxycarbonyl;

aryl($C_1$-$C_4$)alkoxycarbonyl;

(di)($C_1$-$C_4$)(alkyl)aminocarbonyl;

($C_1$-$C_4$)(alkyl)arylaminocarbonyl;

optionally aryl;

5- or 6-membered cationic monocyclic heteroaryl optionally substituted with at least one ($C_1$-$C_4$)alkyl group which may be identical or different;

8- to 11-membered cationic bicyclic heteroaryl optionally substituted with at least one ($C_1$-$C_4$)alkyl group which may be identical or different;

cationic heterocycle of the following formula:

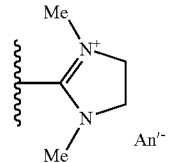

isothiouronium —C(NH$_2$)=N$^+$H$_2$; An'$^-$;

isothiourea —C(NH$_2$)=NH; and

SO$_3^-$; M$^+$ with M$^+$ representing an alkali metal or else An$^-$ of formula (I) and M$^+$ are absent.

6. The fluorescent dye according to claim 1, wherein n=2 and m=0 and a C2 axis of symmetry exists between the two sulfur atoms of the central disulfide radical.

7. The fluorescent dye according to claim 1, comprising at least one of the two formulae (Ia) and (Ib):

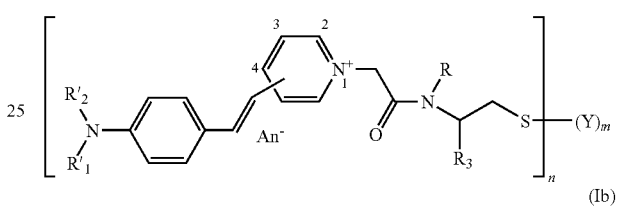

(Ia)

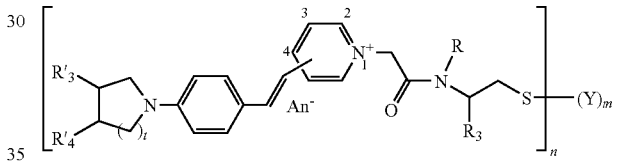

(Ib)

the organic or mineral acid salts, optical isomers and geometric isomers thereof and the solvates such as hydrates;

wherein:

R'$_1$ is chosen from a $C_1$-$C_4$ alkyl group substituted with at least one hydroxyl group or —C(O)—O$^-$;

R'$_2$ is chosen from a $C_1$-$C_4$ alkyl group optionally substituted with at least one hydroxyl group;

R'$_3$ and R'$_4$, which may be identical or different, are chosen from a hydrogen atom, a hydroxyl group, a hydroxy($C_1$-$C_4$)alkyl group, or a —C(O)OR' group, with R' is chosen from a hydrogen atom, a $C_1$-$C_4$ alkyl group, or a —C(O)—O$^-$ group, wherein when R' is a —C(O)—O$^-$ group an anionic counterion An$^-$ is absent, wherein only one of these two radicals R'$_3$ or R'$_4$ can represent a hydrogen atom;

R$_3$ is chosen from a nitrogen atom or a —C(O)OR" group with R" chosen from a hydrogen atom or a $C_1$-$C_4$ alkyl group, or else R$_3$ is chosen from a —C(O)—O$^-$ group and, in this case, an anionic counterion An$^-$ is absent;

a n is an integer ranging from 1 to 2;

m is an integer ranging from 0 to 1;

t is an integer ranging from 1 to 2;

An$^-$ represents an anionic counterion;

Y is chosen from: i) a hydrogen atom; ii) an alkali metal; iii) an alkaline earth metal; iv) an ammonium group: N$^+$R$^\alpha$R$^\beta$R$^\gamma$R$^\delta$, An$^-$ or a phosphonium group: P$^+$R$^\alpha$R$^\beta$R$^\gamma$R$^\delta$, An$^-$ with R$^\alpha$, R$^\beta$, R$^\gamma$ and R$^\delta$, which may be identical or different, are chosen from a hydrogen atom or a ($C_1$-$C_4$)alkyl group, and An$^-$ as defined above; or v) a thiol-function-protecting group;

wherein:
the bond between the pyridinium ring and the double bond of the styryl group is positioned in the 2- or 4-position with respect to the pyridinium;
when n=1, m=1, then Y=H or a thiol-function-protecting group and when n=2, then m=0.

8. The fluorescent dye according to claim 7, wherein when R' is a —C(O)—O⁻ group an anionic counterion An⁻ is absent.

9. The fluorescent dye according to claim 1, chosen from one of the following formulae:

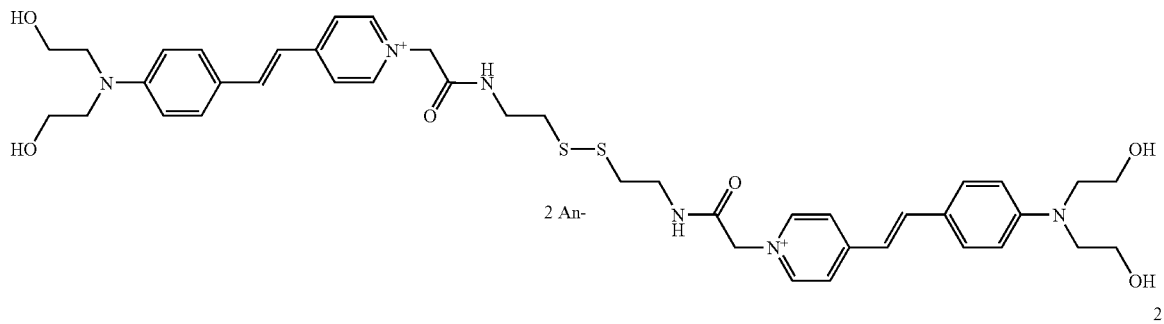

1

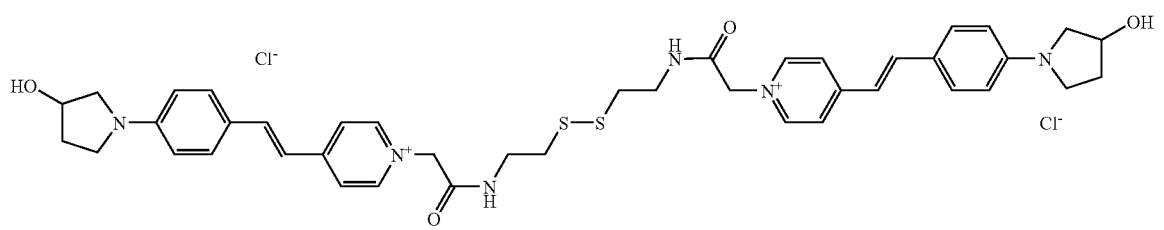

2

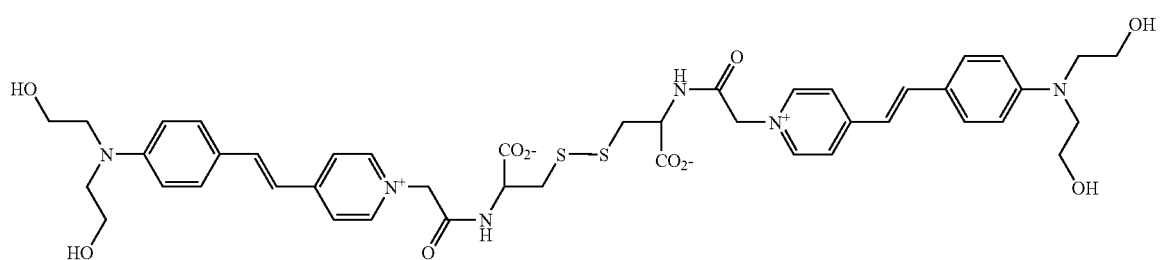

3

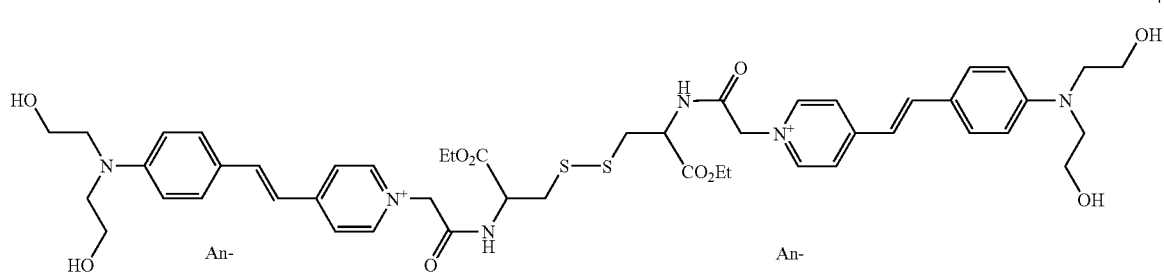

4

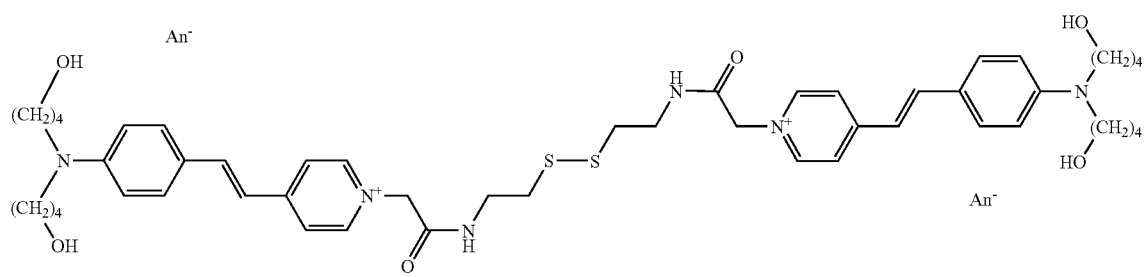

5

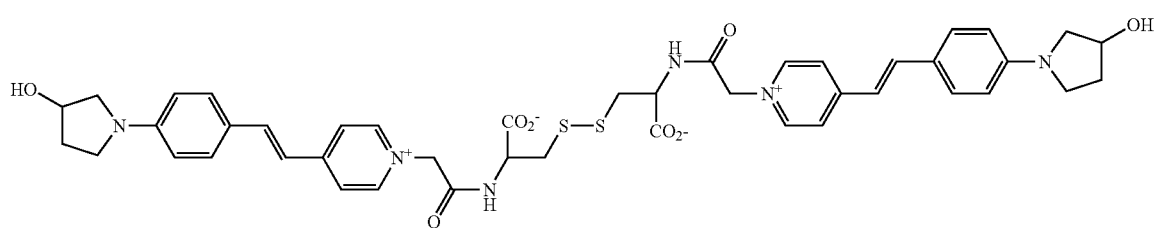
6
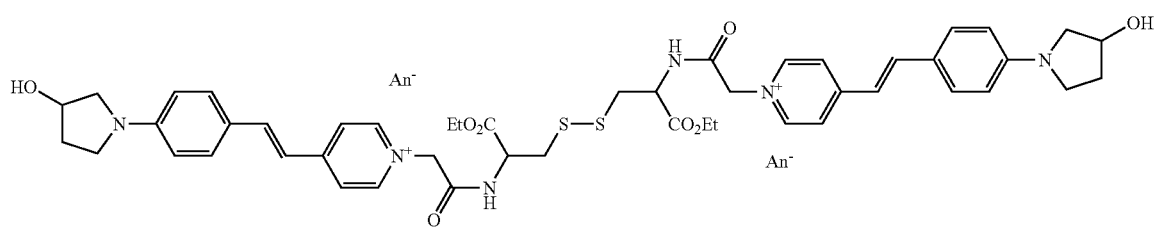
7
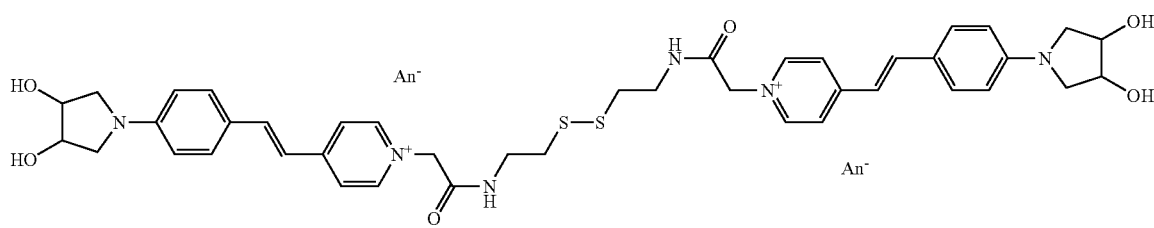
8
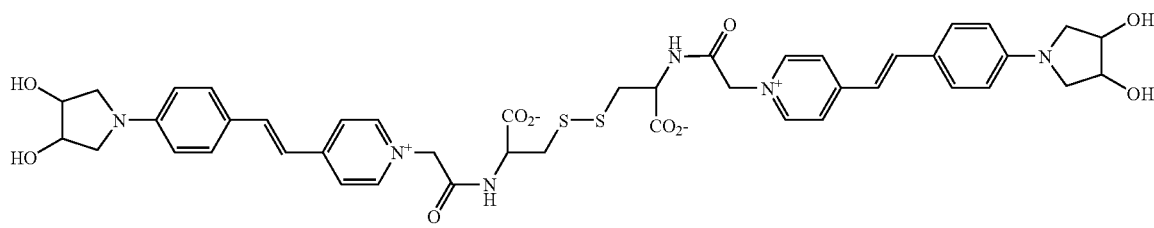
9
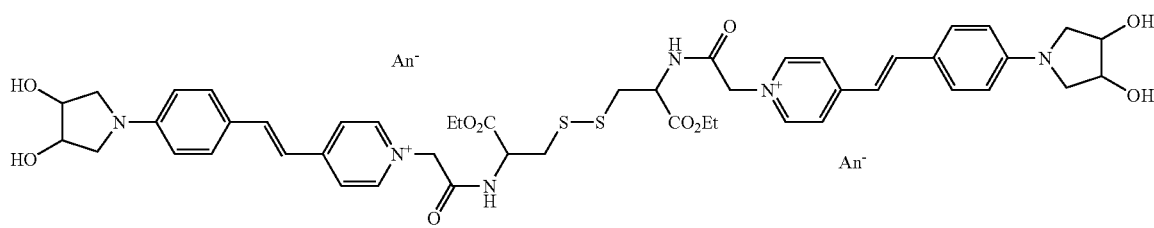
10
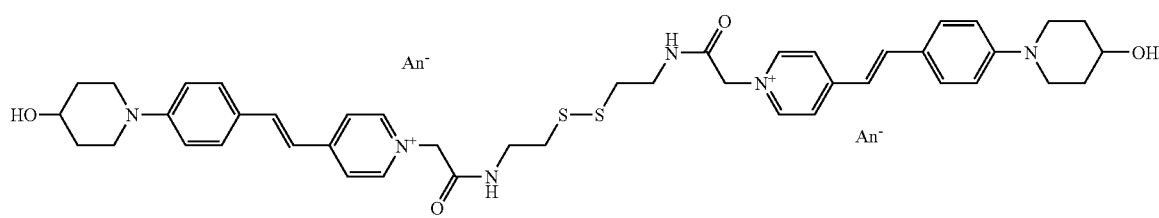
11

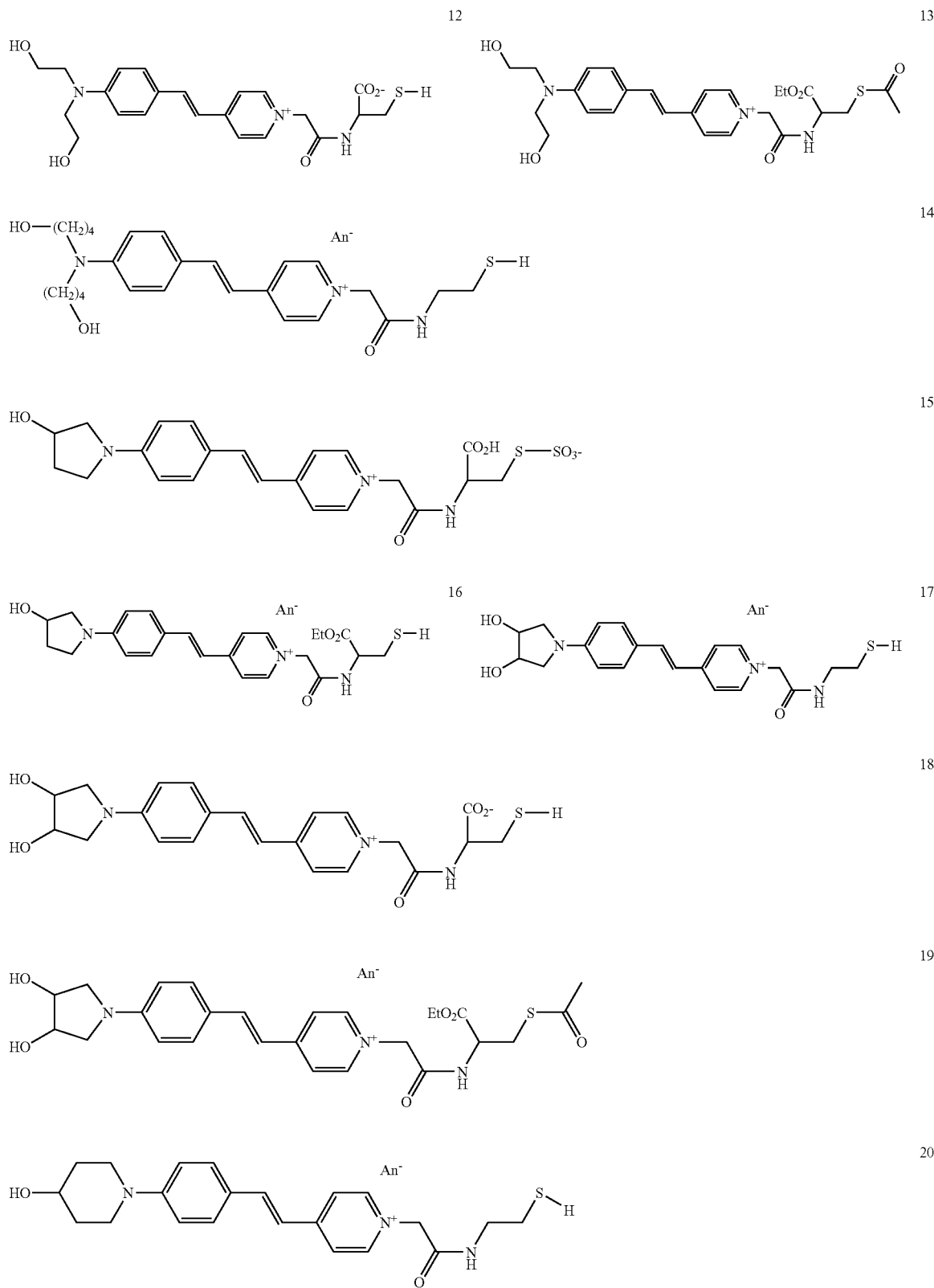

-continued
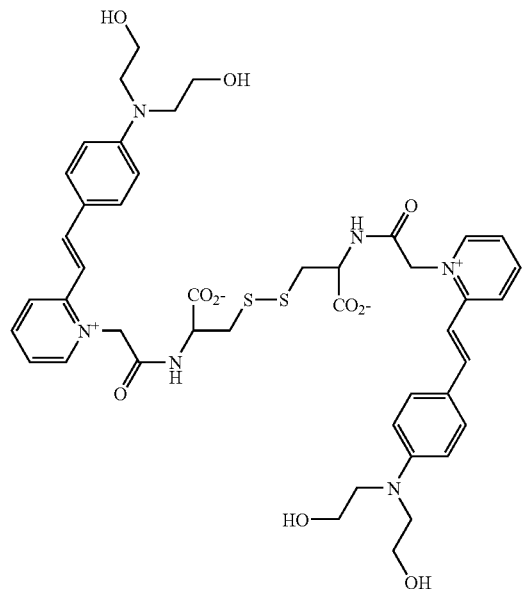
21
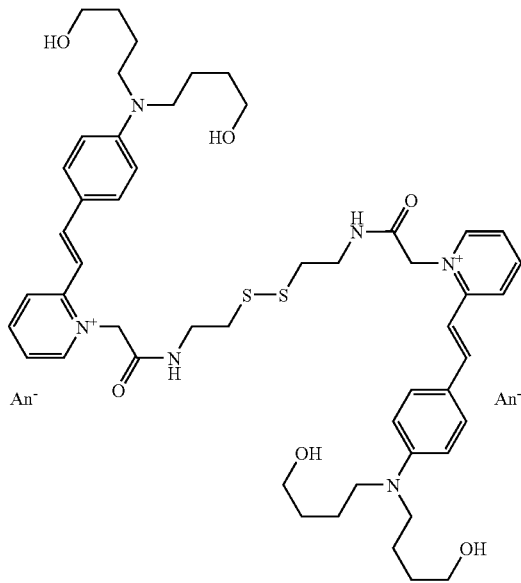
22
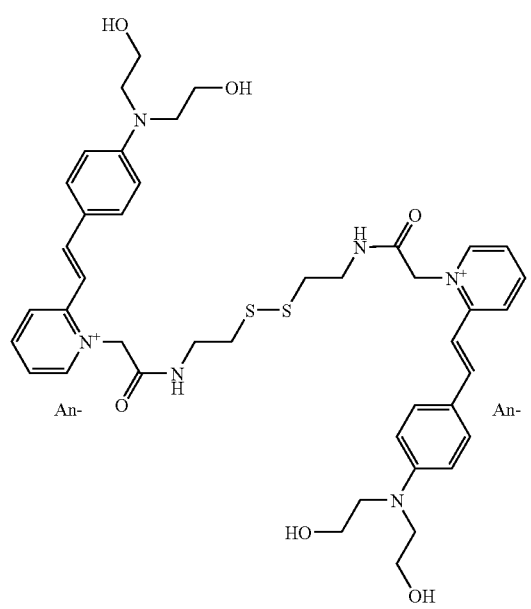
23
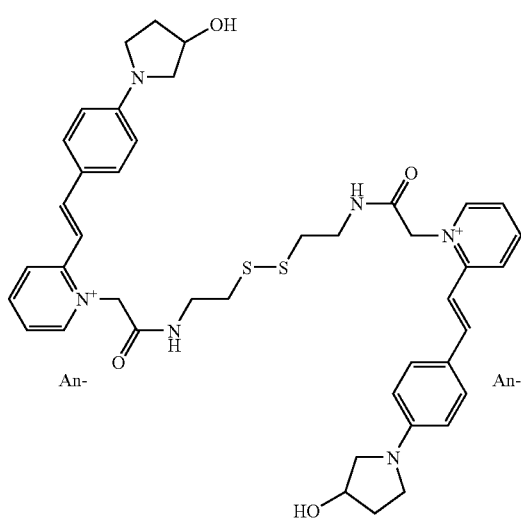
24

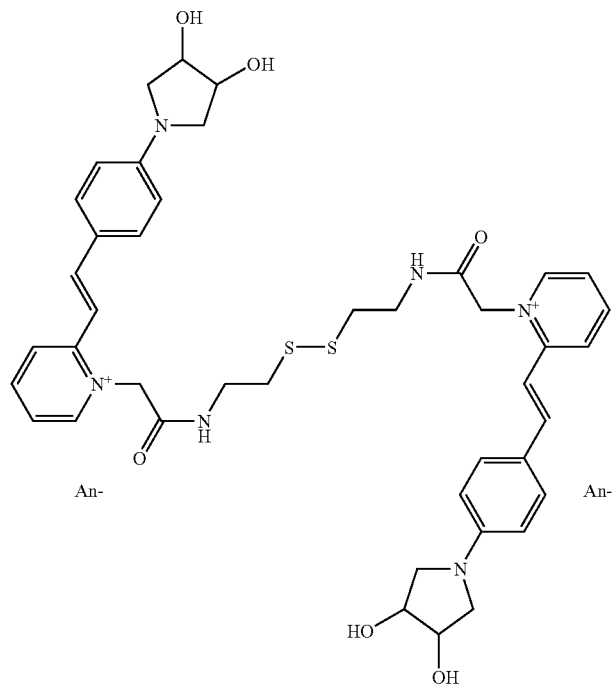
25
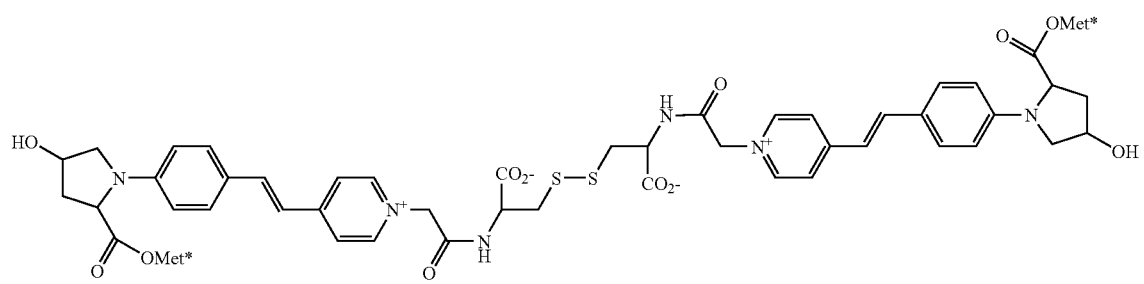
26
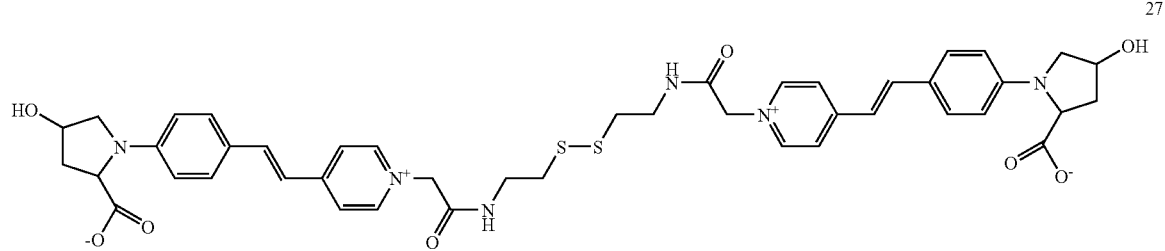
27

-continued
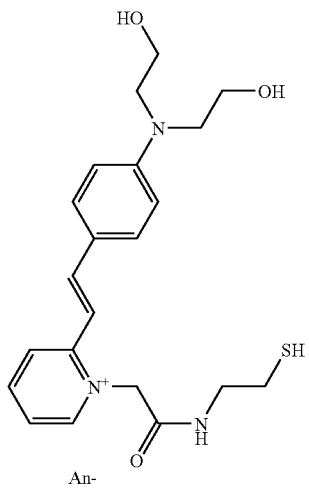
28
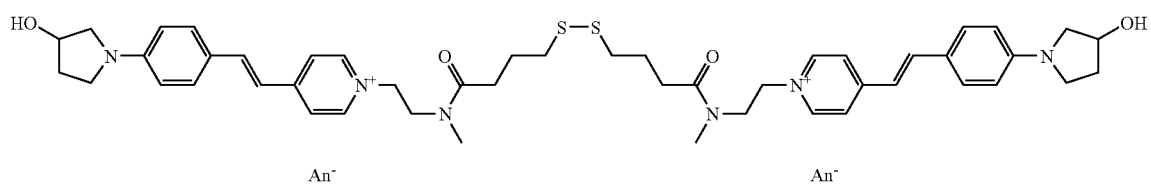
29
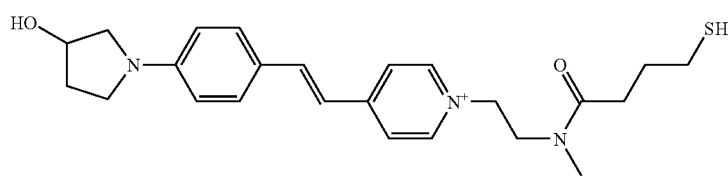
30
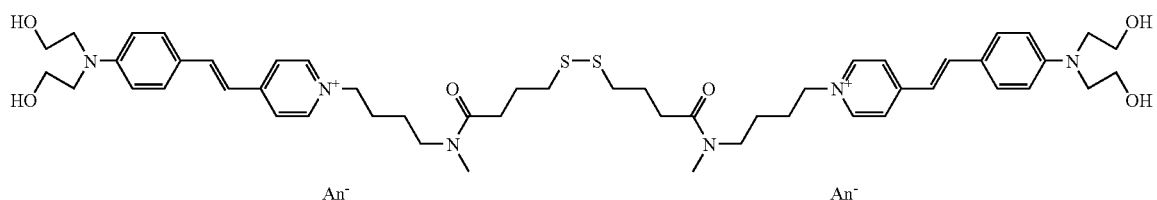
31
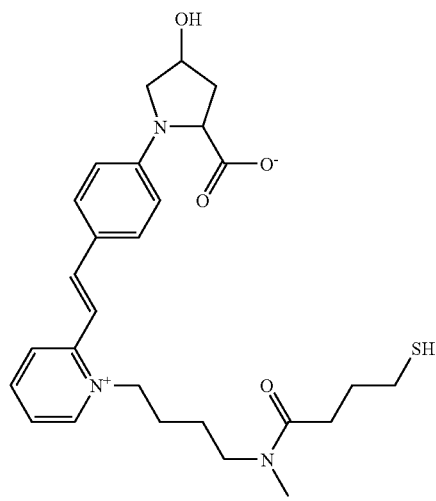
32

-continued

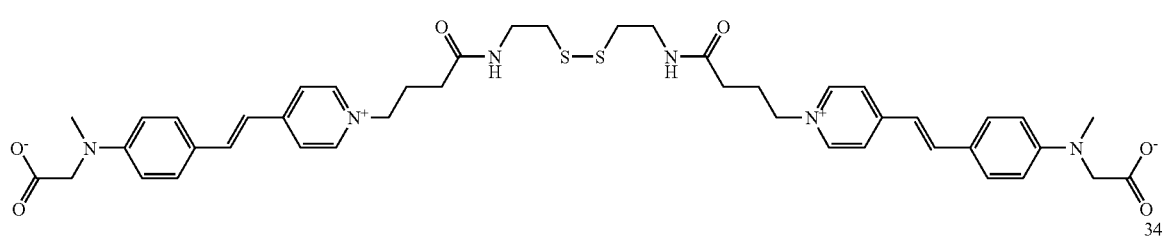

33

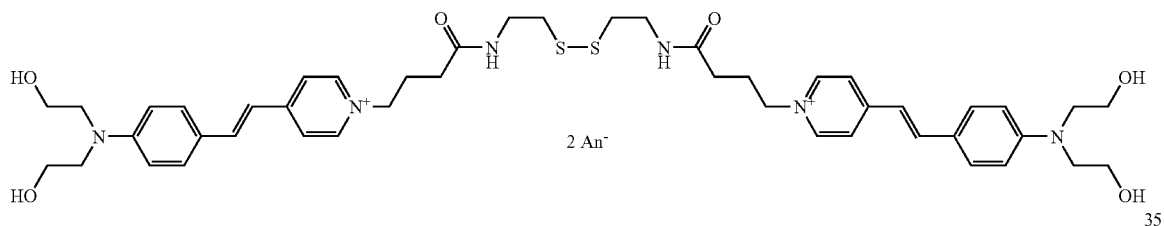

34

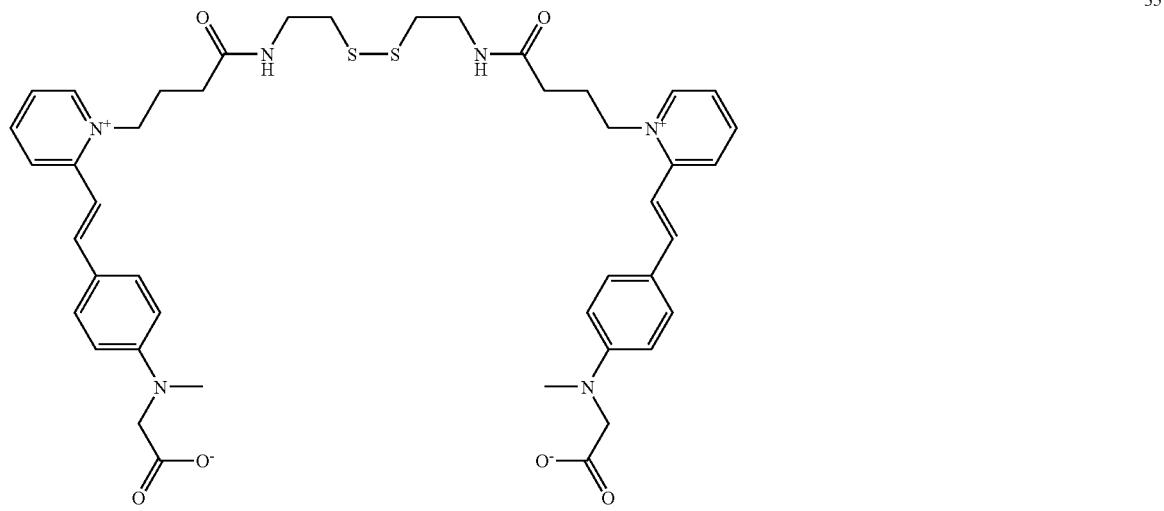

35

36 with An⁻ representing an anionic counterion.

10. A dye composition comprising, in a suitable cosmetic medium, at least one fluorescent dye of formula (I) according to claim 1.

11. A process for dyeing keratin materials comprising applying to the keratin materials a dye composition comprising at least one fluorescent dye of formula (I) according to claim 1, optionally in the presence of a reducing agent.

12. The process according to claim 11, wherein the keratin materials are dark keratin fibers having a tone height of less than or equal to 6.

13. The process according to claim 11, further comprising applying an oxidizing agent to the keratin fibers.

14. A multicompartment device comprising a first compartment and a second compartment,
   wherein the first compartment comprises a dye composition comprising at least one fluorescent dye of formula (I) according to claim 1, and
   the second compartment comprises a reducing agent.

15. A process for dyeing human keratin fibers comprising applying to the keratin fibers a dye composition comprising at least one fluorescent dye of formula (I) as defined in claim 1.

16. The process according to claim 15, wherein the human keratin fibers are dark human keratin fibers having a tone height of less than 6.

17. The process according to claim 15, further comprising applying an oxidizing agent to the keratin fibers.

18. The process according to claim 15, wherein the human keratin fibers are lightened.

19. The process according to claim 16, wherein the human keratin fibers are lightened.

* * * * *

UNITED STATES PATENT AND TRADEMARK OFFICE
CERTIFICATE OF CORRECTION

PATENT NO. : 7,717,964 B2  Page 1 of 1
APPLICATION NO. : 12/234001
DATED : May 18, 2010
INVENTOR(S) : Nicolas Daubresse et al.

It is certified that error appears in the above-identified patent and that said Letters Patent is hereby corrected as shown below:

Claim 7, column 58, line 57, delete "a" before --n is an integer--

Signed and Sealed this

Fifth Day of October, 2010

David J. Kappos
*Director of the United States Patent and Trademark Office*